US 9,868,736 B2

(12) United States Patent
Donato et al.

(10) Patent No.: US 9,868,736 B2
(45) Date of Patent: Jan. 16, 2018

(54) DEUBIQUITINASE INHIBITORS AND METHODS FOR USE OF THE SAME

(71) Applicant: THE REGENTS OF THE UNIVERSITY OF MICHIGAN, Ann Arbor, MI (US)

(72) Inventors: Nicholas J. Donato, Ann Arbor, MI (US); Moshe Talpaz, Ann Arbor, MI (US); Luke Peterson, Ann Arbor, MI (US); Matthew Young, Ann Arbor, MI (US); Hollis D. Showalter, Ann Arbor, MI (US); Christiane Wobus, Dexter, MI (US); Mary Xuan Dziem O'Riordan, Ann Arbor, MI (US); Monika Ermann, Abingdon (GB)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/027,714

(22) PCT Filed: Oct. 10, 2014

(86) PCT No.: PCT/US2014/059997
§ 371 (c)(1),
(2) Date: Apr. 7, 2016

(87) PCT Pub. No.: WO2015/054555
PCT Pub. Date: Apr. 16, 2015

(65) Prior Publication Data
US 2016/0237082 A1 Aug. 18, 2016

Related U.S. Application Data

(60) Provisional application No. 61/889,142, filed on Oct. 10, 2013.

(51) Int. Cl.
C07D 471/04 (2006.01)
C07D 215/14 (2006.01)
C07D 213/57 (2006.01)

(52) U.S. Cl.
CPC ......... C07D 471/04 (2013.01); C07D 213/57 (2013.01); C07D 215/14 (2013.01)

(58) Field of Classification Search
CPC .......................... C07D 471/04; C07D 215/14
See application file for complete search history.

(56) References Cited

U.S. PATENT DOCUMENTS

2012/0077806 A1  3/2012 Donato et al.

FOREIGN PATENT DOCUMENTS

WO   WO-2005/058829 A1   6/2005
WO   WO-2008/005954 A2   1/2008
WO   WO-2011/031884 A2   3/2011
WO   WO-2012/040527 A2   3/2012

OTHER PUBLICATIONS

Bartholomeusz et al., Activation of a novel Bcr/Abl destruction pathway by WP1130 induces apoptosis of chronic myelogenous leukemia cells, Blood, 109(8):3470-8 (2007).
Beroukhim et al., The landscape of somatic copy-number alteration across human cancers, Nature, 463(7283):899-905 (2010).
Dayal et al., Suppression of the deubiquitinating enzyme USP5 causes the accumulation of unanchored polyubiquitin and the activation of p53, J. Biol. Chem., 284(8):5030-41 (2009).
Garcia-Caballero et al., The deubiquitinating enzyme USP5 modulates neuropathic and inflammatory pain by enhancing Cav3.2 channel activity, Neuron., 83(5):1144-58 (2014).
Harris et al., Genetic disruption of USP9X sensitizes colorectal cancer cells to 5-fluorouracil, Cancer Biol. Ther., 13(13):1319-24 (2012).
International Preliminary Report on Patentability, International Application No. PCT/US2014/059997, dated Apr. 12, 2016.
International Search Report and Written Opinion, International Application No. PCT/US2014/059997, dated Jan. 15, 2015.
Jemal et al., Cancer statistics, 2010, CA Cancer J. Clin., 60(5):277-300 (2010).
Kapuria et al., A novel small molecule deubiquitinase inhibitor blocks Jak2 signaling through Jak2 ubiquitination, Cell Signal, 23(12):2076-85 (2011).
Kapuria et al., Deubiquitinase inhibition by small-molecule WP1130 triggers aggresome formation and tumor cell apoptosis, Cancer Res., 70(22):9265-76 (2010).
Lopez-Castejon et al., Deubiquitinases regulate the activity of caspase-1 and interleukin-1β secretion via assembly of the inflammasome, J. Biol. Chem., 288(4):2721-33 (2013).
Naik et al., Regulation of proximal T cell receptor signaling and tolerance induction by deubiquitinase Usp9X, J. Exp. Med., 9 pp. (published Sep. 8, 2014).
Oh et al., Oncogenic Ras and B-Raf proteins positively regulate death receptor 5 expression through co-activation of ERK and JNK signaling, J. Biol. Chem., 287(1):257-67 (2012).
Ozaki et al., p73, a sophisticated p53 family member in the cancer world, Cancer Sci., 96(11):729-37 (2005).
Peng et al., Tyrphostin-like compounds with ubiquitin modulatory activity as possible therapeutic agents for multiple myeloma, Bioorg. Med. Chem., 19(23):7194-204 (2011).
Peterson et al., Mechanism of action of a small molecule inhibitor that targets Usp9x deubiquitinase activity in multiple myeloma and mantle cell lymphoma, 53rd ASH Annual Meeting and Exposition, Abstract 1415(Dec. 10, 2011).

(Continued)

Primary Examiner — Samira Jean-Louis
(74) Attorney, Agent, or Firm — Marshall, Gerstein & Borun LLP

(57) ABSTRACT

Disclosed herein are methods of inhibiting a deubiquitinase (DUB) by contact with a compound of formula (I).

(I)

22 Claims, 7 Drawing Sheets

(56) References Cited

OTHER PUBLICATIONS

Potu et al., Usp5 Links suppression of p53 and FAS levels in melanoma to the BRAF pathway, Oncotarget, 11 pp. (Published Jun. 26, 2014).

Reyes-Turcu et al., Regulation and cellular roles of ubiquitin-specific deubiquitinating enzymes, Annu. Rev. Biochem., 78:363-97 (2009).

Schwickart et al., Deubiquitinase USP9X stabilizes MCL1 and promotes tumour cell survival, Nature, 463(7277):103-7 (2010).

Sun et al., Bcr-Abl ubiquitination and Usp9x inhibition block kinase signaling and promote CML cell apoptosis, Blood, 117(11):3151-62 (2011).

Wuilleme-Toumi et al., Mcl-1 is overexpressed in multiple myeloma and associated with relapse and shorter survival, Leukemia, 19(7):1248-52 (2005).

Yang, Emerging roles of deubiquitinating enzymes in human cancer, Acta Pharmacol. Sin., 28(9):1325-30 (2007).

Extended European Search Report. European patent application No. 14852893.8, dated Mar. 13, 2017.

DEUBIQUITINASE INHIBITORS AND METHODS FOR USE OF THE SAME

CROSS REFERENCE TO RELATED APPLICATIONS

The benefit of U.S. Provisional Application No. 62/889,142, filed Oct. 10, 2013, is claimed, the disclosure of which is incorporated by reference in its entirety herein.

BACKGROUND

Ubiquitination is a covalent post-translational modification of cellular proteins involving a complex enzymatic cascade. Emerging evidence suggests that many enzymes of the ubiquitination cascade are differentially expressed or activated in several diseases, and may therefore be appropriate therapeutic targets.

Protein ubiquitination is a dynamic two-way process that can be reversed or regulated by deubiquitinating (deubiquitinase, DUB) enzymes. The human genome codes for nearly 100 proteins with putative DUB activity which can be broadly divided into two main sub-groups: ubiquitin C-terminal hydrolase (UCH) and the ubiquitin-specific proteases (USP). USPs comprise the largest subclass of DUBs in humans, while only 4 known UCH DUBs have been described. DUBs primarily serve to counterbalance ubiquitin-protein conjugation and also facilitate the cleavage of ubiquitin from its precursors and unanchored polyubiquitin chains. Thus, DUBs regulate and maintain the homeostasis of free ubiquitin pools in the cell. Several DUBs have been reported to regulate deubiquitination of histones, DNA damage repair, cellular proliferation (USP2) and cytokine signaling (DUB-A). DUBs such as USP14, Uch37 and RPN11 have been shown to associate with the regulatory sub-unit of the proteasome (19S) and edit polyubiquitin chains on proteasome substrates.

SUMMARY

Disclosed herein are methods of inhibiting DUBs. Methods are additionally or alternatively directed to inhibiting a UCH catalytic domain. A compound as disclosed herein can inhibit, e.g., Usp9x or Usp5. Further disclosed herein are methods of treating a pathogenic infection and methods of treating a condition due to a pathogenic infection. Also disclosed herein are methods of inhibiting proliferation, decreasing survival of a cell, or suppressing tumor metastases. Further disclosed herein are methods of treating a neurodegenerative disorder or symptoms of a neurodegenerative disorder. Also disclosed herein are methods of treating symptoms of a genetic disorder.

Thus, provided herein is a compound having a formula (I):

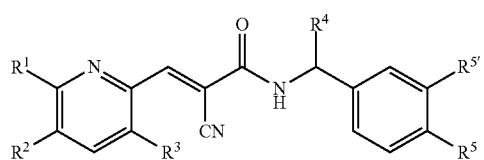

wherein $R^1$ and $R^3$ are halo or hydrogen and $R^2$ is hydrogen, with the proviso that at least one of $R^1$ and $R^3$ is halo, or $R^1$ and $R^2$ together form an aryl or heteroaryl ring, and $R^3$ is halo or hydrogen; $R^4$ is $C_2$-$C_6$alkyl or $C_1$-$C_6$alkylenearyl; and (a) one of $R^5$ and $R^{5'}$ is hydrogen and the other substituted alkoxy, or (b) each of $R^5$ and $R^{5'}$ is substituted alkoxy, or (c) when $R^1$ and $R^2$ together form a substituted aryl or optionally substituted heteroaryl ring, then $R^5$ and $R^{5'}$ can each be hydrogen; or a salt or solvate thereof.

In various cases, $R^1$ and $R^2$ together form a nitrogen-containing optionally substituted heteroaryl. In some cases the compound of formula (I) has a structure

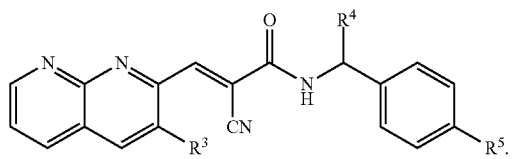

In various cases, $R^4$ is propyl or isopentyl.

In some cases, $R^{5'}$ is hydrogen and $R^5$ is a heterocyclyl substituted alkoxy. In some cases, $R^5$ is —Oalkylene-heterocyclyl. In various cases, $R^5$ is hydrogen and $R^{5'}$ is a heterocyclyl substituted alkoxy. $R^{5'}$ can be —Oalkylene-heterocyclyl. In various cases, the heterocyclyl is morpholinyl, sulfoxymorpholinyl, pyrrolidinyl, piperazinyl, or piperidinyl. In some cases, the heterocyclyl is morpholinyl. In various cases, $R^5$ or $R^{5'}$ is —O($CH_2$)$_m$N(Me)($CH_2$)$_2$N$Me_2$; —O($CH_2$)$_m$N(Me)($CH_2$)$_2$NHMe; —O($CH_2$)$_m$N(Me)($CH_2$)$_2$NEt$_2$; —O($CH_2$)$_m$N(Me)($CH_2$)$_2$NHEt; —O($CH_2$)$_m$O($CH_2$)$_2$N$Me_2$; —O($CH_2$)$_m$O($CH_2$)$_2$NHMe; —O($CH_2$)$_m$O($CH_2$)$_2$NEt$_2$; or —O($CH_2$)$_m$O($CH_2$)$_2$NHEt, and m is 1, 2, 3, 4, 5, 6, 7, 8, 9, or 10.

In various cases, $R^1$ and $R^3$ are each halo. In some cases, $R^1$ and $R^3$ are the same. In various cases, $R^1$ and $R^3$ are different. In some cases, at least one of $R^1$ and $R^3$ is chloro. In various cases, each of $R^1$ and $R^3$ is chloro. In some cases, at least one of $R^1$ and $R^3$ is fluoro. In some cases, each of $R^1$ and $R^3$ is fluoro.

The compound of formula (I) can have a structure

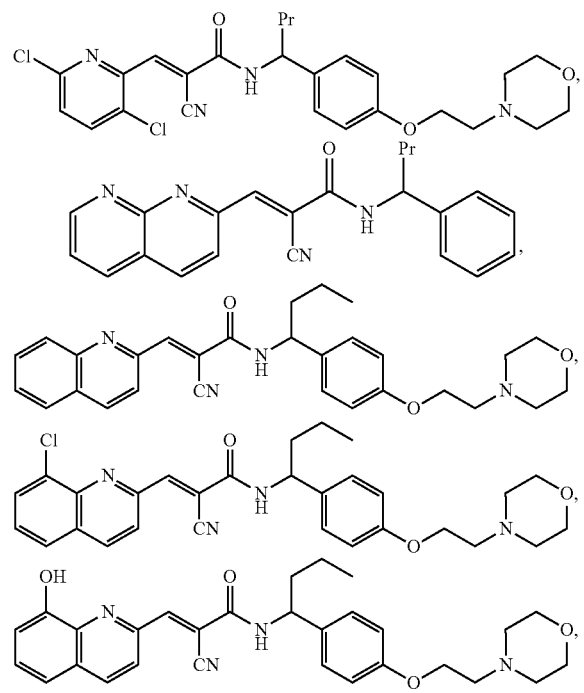

-continued

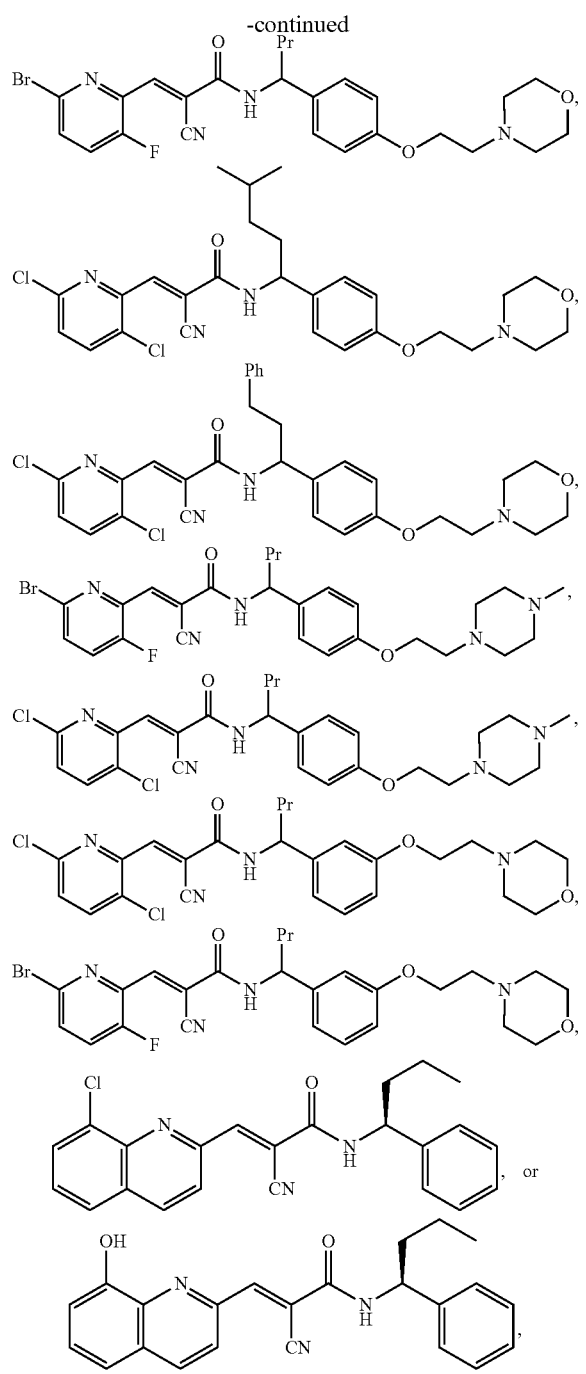

or a salt or solvate thereof.

Further discloses is a compound having a structure

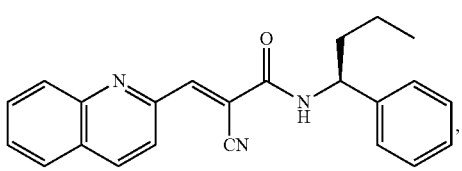 [SMILES: CCC[C@H](NC(=O)/C(C#N)=C/c1ccc2ccccc2n1)c1ccccc1]

or a salt or solvate thereof.

Also disclosed are pharmaceutical compositions comprising a compound as described herein and a pharmaceutically acceptable excipient. The pharmaceutical composition can be formulated for oral, topical, intravenous, subcutaneous, intramuscular, intrathecal, ophthalmic, or inhalational route of administration.

Additionally provided are methods of inhibiting proliferation in a cell comprising contacting the cell with the compound or composition as disclosed herein. The cell can be a cancer cell, e.g., a virus-induced cancer cell, a Kaposi's sarcoma cell, a nasopharyngeal carcinoma (EBV) cell, a chronic myelogenous leukemia (CML) cell, a melanoma cell, an acute lymphocytic leukemia cell, a chronic lymphocytic leukemia cell, an acute myelogenous leukemia cell, a B-cell lymphoma cell, a mantle cell lymphoma cell, a multiple myeloma cell, a plasma cell dyscrasia, a myeloproliferative disorder cell, or a glioblastoma cell. The cell can be a lung cancer cell, a breast cancer cell, a prostate cancer cell, a pancreatic cancer cell, a melanoma cell, a solid tumor cell, or a colon cancer cell. The compound can inhibit a DUB, e.g., a UCH catalytic domain of a DUB. The DUB can be Usp9x. The DUB can be Usp5.

Further provided are methods of inhibiting a DUB comprising contacting the DUB with a compound or composition as disclosed herein.

Also provided are methods of inhibiting a pathogen infection comprising contacting a pathogen or a cell infected with a pathogen with the compound or composition as disclosed herein. Additionally provided are methods of treating a condition arising from a pathogen infection comprising contacting the pathogen or a cell infected by the pathogen with the compound or composition as disclosed herein. The condition can be gastroenteritis, encephalitis, a respiratory tract infection, SARS, virus-induced cancer, rabies, a hemorrhagic fever, Rift valley fever, listeriosis, or toxoplasmosis. In some cases, the condition is meningitis, myocarditis, hepatitis, bacterimia, or a skin infection. The pathogen can be a virus, bacterium, fungus, or parasite. The virus can be a calicivirus, a norovirus, a sapovirus, a picornavirus, a Togavirus, a Bunyavirus, a Rhabdovirus, a herpes virus, an adenovirus, an arterivirus, a coronavirus, a flavivirus, a paramyxovirus, a papillomavirus, a virus encoding for an ovarian tumor (OTU)-like protease, a baculovirus, or a nairovirus. The virus can be a polyoma virus or a retrovirus. In various cases, the virus is selected from the group consisting of encephalomyocarditis virus (EMCV), Sindbis virus (SiNV), La Crosse virus (LaCV), Norwalk virus, Epstein-Barr (EBV), herpesvirus, Dengue virus, and papillomavirus. The virus can be cytomegalovirus, BK virus, hepatitis C virus, or HIV. The bacterium can be *Chlamydia, Escherichia, Salmonella, Yersinia, Burkholderia, Haemophilus, Listeria,* or *Mycobacterium*. In some cases, the bacterium is *Staphylococcus aureus*. In various cases, the bacterium is methicillin-resistant *Staph aureus* (MRSA). The parasite or fungus can be *Plasmodium falciparum, Toxoplasma gondii, Entamoeba histolytica, Giardia lamblia, Trypanosoma brucei, Trypanosoma cruzi, Cestoda, Clonorchis, Opisthorchis, Strongylocides, Candida, Aspergillus,* or *Cryptococcus*.

DETAILED DESCRIPTION

Figure 1:
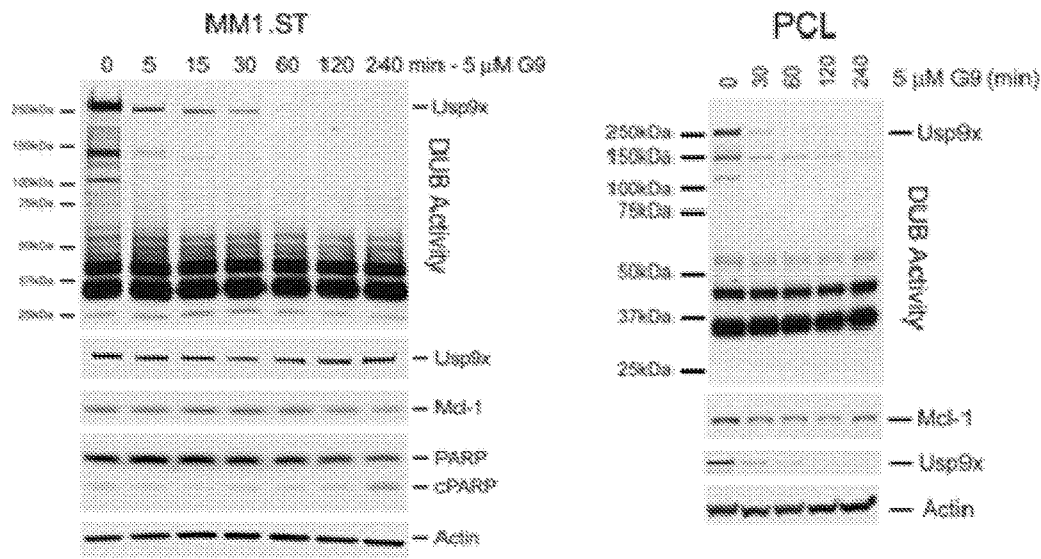
FIG. 1 shows that G9 rapidly inactivates Usp9x in tumor cells. MM1.ST myeloma cells (left) and PCL cells from a patient donor (right) were treated with G9 for the time indicated before cell lysates were assessed for Usp9x activity and Mcl-1 levels. PARP was also measured in MM1.ST cells as a marker of the activation of caspases and apoptosis.

Protein ubiquitination is a precisely controlled process that requires the participation of several enzymes that modify lysine residues on target proteins with monomeric or polymeric chains of ubiquitin (Ub). The ubiquitin pathway enzymes are mediators of eukaryotic cell cycle timing, protein destruction and signal transduction. Recent studies suggest that Ub regulation is also critical at various stages of the prokaryotic and viral life cycle and within the eukaryotic host cells as well. Therefore, disruption or inhibition of specific Ub regulatory enzymes may also have anti-microbial activity.

Owing to the diverse role of DUBs in the regulation of proteins involved in transformation, cell cycle regulation, apoptotic protection and drug resistance, DUBs appear to represent appropriate therapeutic targets. Recently, down regulation of USP2 and USP9x were shown to inhibit tumor cell growth by promoting cyclin D1 and MCL-1 degradation, respectively suggesting silencing of specific DUBs in tumor cells may be a safe and effective therapy in oncogene-addicted or drug-resistant cells. Other studies firmly establish a role for DUBs in a broad spectrum of diseases including cancer, viral and bacterial pathogenesis as well as neurodegenerative disorders. Although few compounds have been described with DUB modulatory activity, most report anti-tumor, anti-proliferative or anti-viral activity associated with DUB inhibition (e.g., UCH-L1 and USP7, SARS protease).

In addition, Usp5 regulates unanchored poly-ubiquitin (Ub) chains, p53 transcriptional activity and double-strand DNA repair. Knockdown and overexpression studies show that Usp5 regulates p53 (and p73) levels and alters cell growth and cell cycle distribution associated with p21 induction. Usp5 also regulates the intrinsic apoptotic pathway by modulating p53-dependent FAS expression. Usp5 inhibition can provide an alternate approach in recovery of diminished p53 (or p73) function in melanoma and can add to the targeted therapies already used in the treatment of melanoma.

Thus, disclosed herein are methods of inhibiting a DUB, methods of inhibiting a UCH catalytic domain, methods of inhibiting Usp9x, methods of inhibiting Usp5, methods of inhibiting or preventing a pathogenic infection, methods of inhibiting survival or proliferation of a cell, methods of treating a neurodegenerative disorder, methods of treating one or more symptoms of a neurodegenerative disorder, methods of treating one or more symptoms of a genetic disorder, and compounds that can inhibit a DUB. In methods provided, the DUB is contacted with a compound, e.g., of formula (I) or salt thereof

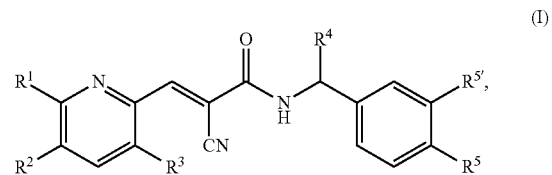

wherein $R^1$ and $R^3$ are each independently halo or hydrogen with the proviso that at least one of $R^1$ and $R^3$ is not hydrogen, $R^2$ is hydrogen, or $R^1$ and $R^2$ together form a substituted aryl or an optionally substituted heteroaryl ring, $R^4$ is $C_2$-$C_6$alkyl or $C_1$-$C_6$alkylenearyl; and one of $R^5$ and $R^{5'}$ is hydrogen and the other substituted alkoxy, or each of $R^5$ and $R^{5'}$ is substituted alkoxyl, or when $R^1$ and $R^2$ together form an optionally substituted hetearyl ring or substituted aryl ring, $R^5$ and $R^{5'}$ can alternatively each be hydrogen;

or a salt or solvate thereof. In various cases, the compound has a structure of

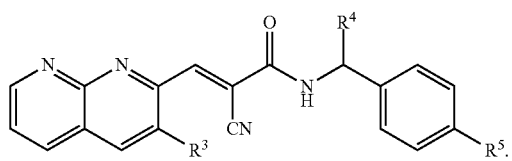

In some cases, $R^1$ and $R^3$ are each halo, e.g., selected from chloro, bromo, iodo, and fluoro. In various cases, $R^4$ is propyl, isopentyl, or phenethyl. In various cases, $R^5$ is alkoxy substituted with a heterocyclyl, e.g., —Oalkylene-heterocyclyl. In various cases, the heterocyclyl is morpholinyl, sulfoxymorpholinyl, pyrrolidinyl, piperazinyl, or piperidinyl. In some cases, the heterocyclyl is a morpholinyl group. In various cases, $R^5$ is —O(CH$_2$)$_m$N(Me)(CH$_2$)$_2$NMe$_2$; —O(CH$_2$)$_m$N(Me)(CH$_2$)$_2$NHMe; —O(CH$_2$)$_m$N(Me)(CH$_2$)$_2$NEt$_2$; —O(CH$_2$)$_m$N(Me)(CH$_2$)$_2$NHEt; —O(CH$_2$)$_m$O(CH$_2$)$_2$NMe$_2$; —O(CH$_2$)$_m$O(CH$_2$)$_2$NHMe; —O(CH$_2$)$_m$O(CH$_2$)$_2$NEt$_2$; or —O(CH$_2$)$_m$O(CH$_2$)$_2$NHEt, and m is 1, 2, 3, 4, 5, 6, 7, 8, 9, or 10. In some cases, the compound is

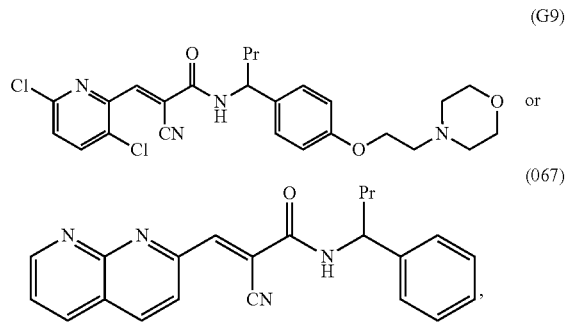

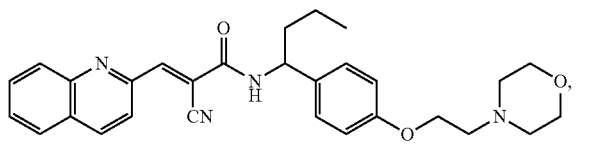

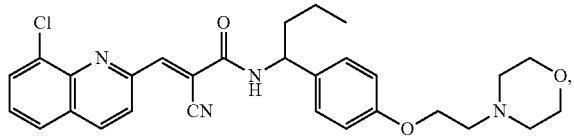

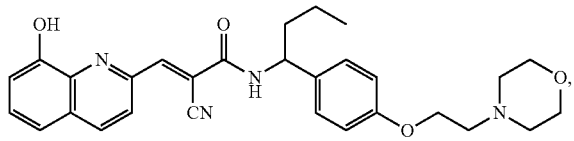

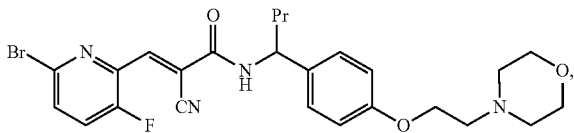

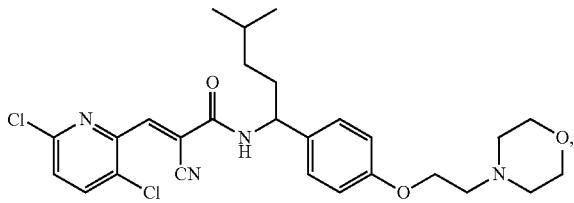

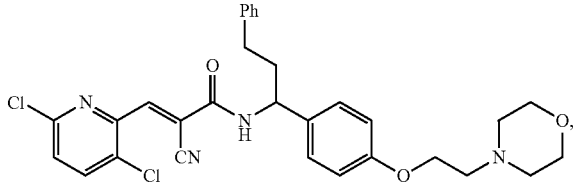

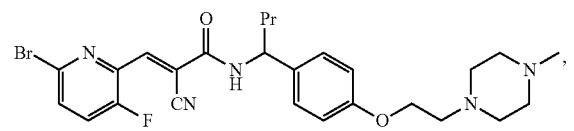

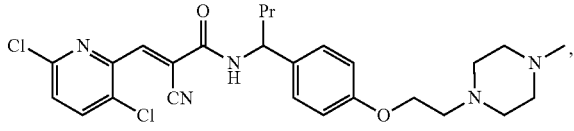

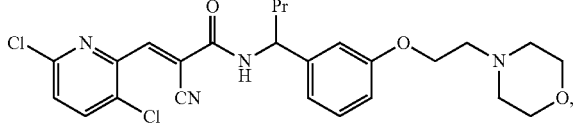

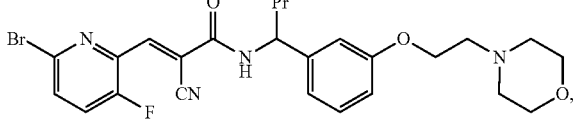

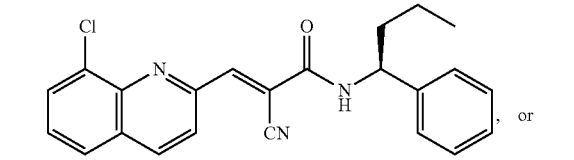, or

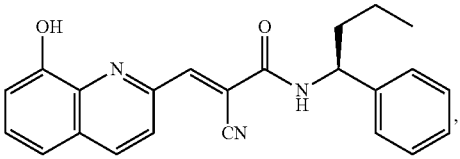

or a salt or solvate thereof. In various cases, the DUB inhibitor has a structure of

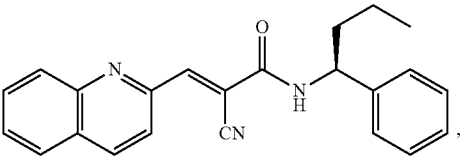 [SMILES: CCC[C@H](NC(=O)/C(C#N)=C/c1ccc2ccccc2n1)c1ccccc1]

or a salt or solvate thereof.

Chemical Synthesis

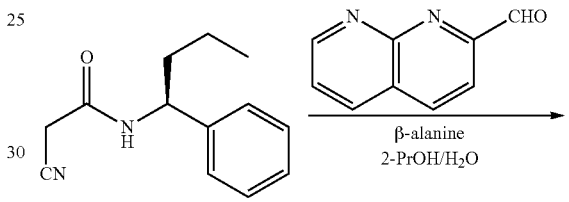

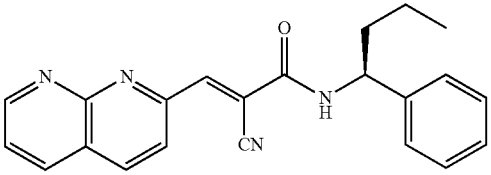

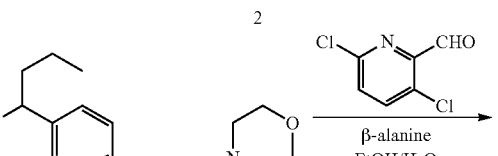

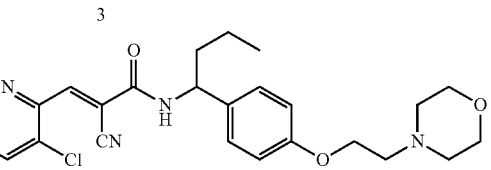

(S,E)-2-Cyano-3-(1,8-naphthyridin-2-yl)-N-(1-phenylbutyl)acrylamide (2) A solution of 1,8-naphthyridine-2-carbaldehyde (73.1 mg, 0.46 mmol), (S)-2-cyano-N-(1-phenylbutyl)acetamide (Donato N J, Wobus C, Showalter H D H, Talpaz M, Perry J W, Sorenson R J, O'Riordan M X D, Jin Y. Deubiquitinase Inhibitors and Methods for Use of the Same. WO 2012040527; 1; 50 mg, 0.23 mmol), β-alanine (165 mg, 1.85 mmol), 2-propanol (6 mL) and water (3 mL). was stirred under nitrogen at room temperature for 18 h. The mixture was diluted with water and extracted with ethyl acetate. The combined extracts were washed twice with water, saturated brine, dried over sodium sulfate and concentrated to leave a yellow film. Purification by preparative thick layer chromatography, eluting with 1.5% methanol in dichloromethane provided 2 (34.1 mg, 41%) as a yellow foam: $^1$H NMR (500 MHz, chloroform-d) δ 9.25 (d, J=4.2 Hz, 1H), 8.53 (s, 1H), 8.34 (d, J=8.3 Hz, 1H), 8.25 (d, J=8.1 Hz, 1H), 7.91 (d, J=8.3 Hz, 1H), 7.58 (dd, J=8.2, 4.2 Hz, 1H), 7.38-7.25 (m, 5H), 6.85 (d, J=8.1 Hz, 1H), 5.11 (q, J=7.7 Hz, 1H), 1.99-1.83 (m, 2H), 1.38 (m, 2H), 0.97 (t, J=7.3 Hz, 3H); MS (ES$^+$) m/z 357.3 (M+H)$^+$.

(E)-2-Cyano-3-(3,6-dichloropyridin-2-yl)-N-(1-(4-(2-morpholinoethoxy)phenyl)butyl)acrylamide (4). This compound was synthesized from 3,6-dichloropicolinaldehyde and 2-cyano-N-(1-(4-(2-morpholinoethoxy)phenyl)butyl) acetamide (3; Donato N J, Wobus C, Showalter H D H, Talpaz M, Perry J W, Sorenson R J, O'Riordan M X D, Jin Y. Deubiquitinase Inhibitors and Methods for Use of the Same. WO 2012040527), β-alanine, and aqueous ethanol by the previously described generalized procedure (Donato N J, Wobus C, Showalter H D H, Talpaz M, Perry J W, Sorenson R J, O'Riordan M X D, Jin Y. Deubiquitinase Inhibitors and Methods for Use of the Same. WO 2012040527): $^1$H NMR (400 MHz, chloroform-d) δ 8.61 (s, 1H), 7.74 (d, J=8.5 Hz, 1H), 7.38 (d, J=8.5 Hz, 1H), 7.24 (d, 2H), 6.89 (d, J=8.7 Hz, 2H), 6.78 (d, J=7.8 Hz, 1H), 5.01 (q, J=7.6 Hz, 1H), 4.10 (t, J=5.7 Hz, 2H), 3.78-3.71 (m, 4H), 2.80 (t, J=5.7 Hz, 2H), 2.60-2.55 (m, 4H), 1.96-1.76 (m, 2H), 1.41-1.30 (m, 2H), 0.95 (t, J=7.4 Hz, 3H); MS (ES$^-$) m/z 501.3 (M–H$^+$/503.4 (M–H)$^+$ (3:1 Cl isotope pattern).

Deubiquitinases (DUBs)

Deubiquitinating enzymes (i.e., deubiquitinases or DUBs) are typically a cysteine protease and may be classified into subgroups as ubiquitin-specific proteases (USP) and ubiquitin C-terminal hydrolases (UCH). Examples of DUBs include, for instance, USP5, USP6, USP4, USP8, USP13, USP2, USP11, USP14, USP7, USP9X, USP10, USP1, USP12, USP16, USP15, USP17, USP19, USP20, USP3, USP9Y, USP18, USP21, USP22, USP33, USP29, USP25, USP36, USP32, USP26, USP24, USP42, USP46, USP37, USP28, USP47, USP38, USP44, USP50, USP35, USP30, Mername-AA088peptidase, Mername-AA091 peptidase, USP45, USP51, USP34, USP48, USP40, USP31, Mername-AA129peptidase, USP49, USP17-like peptidase, USP54, USP53, USP39, UCH-L1, UCH-L3, UCH-BAP1, UCH37, Cezanne deubiquitinating peptidase, Cezanne2, tumor necrosis factor alpha-induced protein 3, TRABID protein, VCP(p97)/p47-interacting protein, otubain1, otubain2, Cy1D protein, SENP1 peptidase, SENP3 peptidase, SENP6 peptidase, SENP2 peptidase, SENP5peptidase, SENP7peptidase, SENP8peptidase, SENP4peptidase, Pohl peptidase, Jab1/MPN domain metalloenzyme, Mername-AA 165 peptidase, Mername-AA 166 peptidase, Mername-AA 167 peptidase, Mername-AA168 protein, COPS signalosome subunit6, 26S proteasome non-ATPase regulatory subunit7, eukaryotic translation initiation factor3 subunit5, IFP38 peptidase homologue. In some cases, the DUB inhibited by a compound as disclosed herein is Usp9x. In various cases, the DUB inhibited by a compound as disclosed herein is Usp5.

Other DUBs contemplated include autophagin (ATG), ovarian tumor (OTU) domain proteins, Josephin-domain (JD) or Machado-Joseph disease (MJD) proteins, ubiquitin-like protein-specific protease (ULP), and JAMM (Jab1/MPN domain-associated metalloisopeptidase) domain proteins.

Specific DUB Inhibitors

Compounds that are used in methods disclosed herein include compounds, or salts thereof, of formula (I)

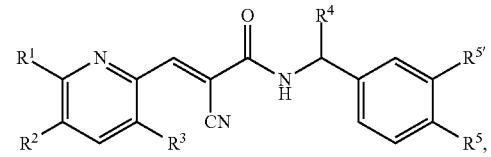

wherein
R$^1$ and R$^3$ are each independently hydrogen or halo with the proviso that at least one of R$^1$ and R$^3$ is not hydrogen,
R$^2$ is hydrogen, or R$^1$ and R$^2$ together form a substituted aryl or an optionally substituted heteroaryl ring,
R$^4$ is C$_2$-C$_6$alkyl or C$_1$-C$_6$alkylenearyl; and
one of R$^5$ and R$^{5'}$ is hydrogen and the other substituted alkoxy, or each of R$^5$ and R$^{5'}$ is substituted alkoxyl, or when R$^1$ and R$^2$ together form an optionally substituted heteraryl ring or substituted aryl ring, R$^5$ and R$^{5'}$ can alternatively each be hydrogen; or more specifically is a compound having a structure of

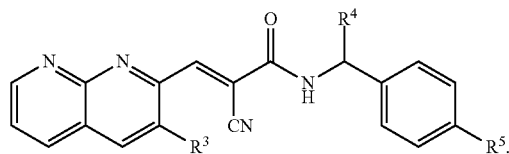

In various cases, when R$^1$ and R$^2$ form a heteroaryl ring, the heteroaryl ring is substituted. In more specific cases, the heteroaryl ring is substituted with one or more of OH, halo, cyano, and nitro. In various cases, when R$^1$ and R$^2$ form a substituted aryl ring, the aryl ring is substituted with one or more of OH, halo, cyano, and nitro. In some cases, R$^1$ and R$^3$ are each halo, e.g., selected from chloro, bromo, iodo, and fluoro. In various cases, R$^4$ is phenethyl. In various cases, R$^4$ is propyl or isopentyl. In some cases, R$^5$ is hydrogen and R$^{5'}$ is substituted alkoxy, e.g., alkoxy substituted with a heterocyclyl, e.g., —Oalkyleneheterocyclyl. In various cases, R$^{5'}$ is hydrogen and R$^5$ is alkoxy substituted with a heterocyclyl, e.g., —Oalkyleneheterocyclyl. In various cases, the heterocyclyl is morpholinyl, sulfoxymorpholinyl, pyrrolidinyl, piperazinyl, or piperidinyl. In some cases, the heterocyclyl is a morpholinyl group. In various cases, R$^5$ or R$^{5'}$ is —O(CH$_2$)$_m$N(Me)(CH$_2$)$_2$NMe$_2$; —O(CH$_2$)$_m$N(Me) (CH$_2$)$_2$NHMe; —O(CH$_2$)$_m$N(Me)(CH$_2$)$_2$NEt$_2$; —O(CH$_2$)$_m$ N(Me)(CH$_2$)$_2$NHEt; —O(CH$_2$)$_m$O(CH$_2$)$_2$NMe$_2$; —O(CH$_2$)$_m$ O(CH$_2$)$_2$NHMe; —O(CH$_2$)$_m$O(CH$_2$)$_2$NEt$_2$; or —O(CH$_2$)$_m$O(CH$_2$)$_2$NHEt, and m is 1, 2, 3, 4, 5, 6, 7, 8, 9, or 10.

In some cases, the DUB inhibitor is

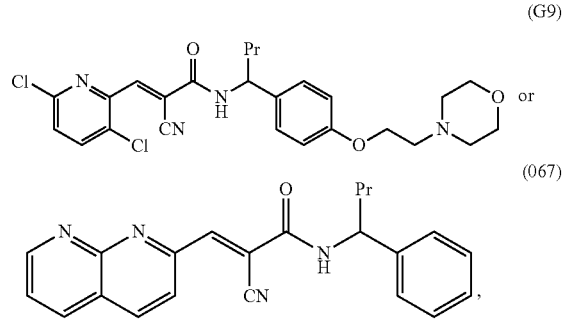

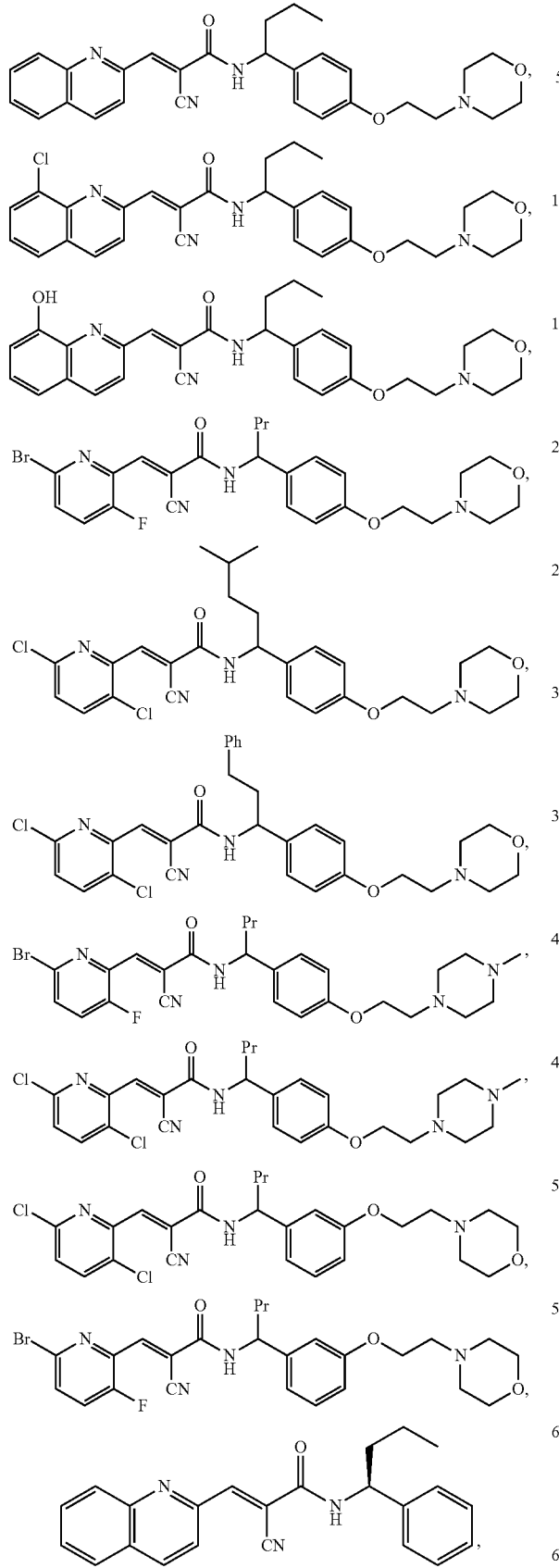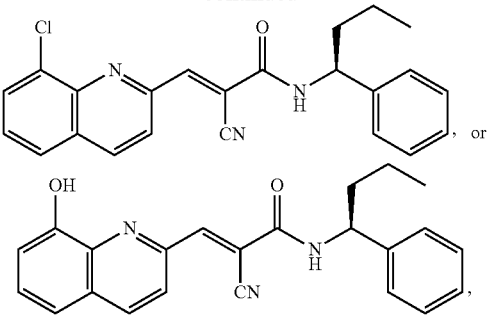

or a salt or solvate thereof.

The term "alkyl" refers to a saturated or unsaturated straight or branched chain hydrocarbon group including, but not limited to, methyl, ethyl, n-propyl, isopropyl, n-butyl, isobutyl, tert-butyl, pentyl, isopentyl, n-hexyl, and the like. Alkyls of one to six carbon atoms are also contemplated. The term "alkyl" includes "bridged alkyl," i.e., a bicyclic or polycyclic hydrocarbon group, for example, norbornyl, adamantyl, bicyclo[2.2.2]octyl, bicyclo[2.2.1]heptyl, bicyclo [3.2.1]octyl, or decahydronaphthyl. Alkyl groups optionally can be substituted, for example, with one or more of hydroxy (OH), halide, thiol (SH), aryl, heteroaryl, cycloalkyl, heterocyclyl, and amino.

The term "cycloalkyl" refers to a cyclic hydrocarbon group, e.g., cyclopropyl, cyclobutyl, cyclohexyl, and cyclopentyl. "Heterocyclyl" is defined similarly as cycloalkyl, except the ring contains one to three heteroatoms independently selected from the group consisting of oxygen, nitrogen, and sulfur. Nonlimiting examples of heterocyclyl groups include piperdine, tetrahydrofuran, tetrahydropyran, dihydrofuran, morpholine, thiophene, and the like. Cycloalkyl and heterocyclyl groups can be saturated or partially unsaturated ring systems optionally substituted with, for example, one to three groups, independently selected from the group consisting of alkyl, alkyleneOH, $C(O)NH_2$, $NH_2$, oxo (=O), aryl, haloalkyl, halo, and OH. Heterocycloalkyl groups optionally can be further N-substituted with alkyl, hydroxyalkyl, alkylenearyl, or alkyleneheteroaryl.

The term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

The term "heteroaryl" refers to a monocyclic or bicyclic ring system containing one or two aromatic rings and containing at least one nitrogen, oxygen, or sulfur atom in an aromatic ring. The ring can be fused or spiro to another ring system (a saturated, unsaturated or aromatic ring). Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. In some cases, the heteroaryl group is substituted with one or more of alkyl and alkoxy groups.

Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, pyrollyl, imidazolyl, benzothiazolyl, pyrazinyl, pyrimidinyl, thiazolyl, and thiadiazolyl.

The term "alkoxy" refers to straight or branched chain alkyl group covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The salts, e.g., pharmaceutically acceptable salts, of the disclosed therapeutics may be prepared by reacting the appropriate base or acid with a stoichiometric equivalent of the therapeutic.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Methods of Treatment

Methods disclosed herein include methods of treating a disorder, such as a disorder associated with DUB activity or a disorder affected by modulation of DUB activity, or use of a compound disclosed herein in the preparation of a medicament to treat a disorder associated with DUB activity and/or affected by modulation of DUB activity. Further contemplated are methods of treatment wherein a UCH catalytic domain is inhibited. Specific disorders contemplated include pathogenic infections, cancer, developmental and neurodegenerative disorders, Riddle syndrome, Parkinson's disease, Alzheimer's Disease, and genetic disorders requiring or modulated by DUBs, e.g. Fanconi anemia.

In some cases, provided herein are methods that further include identifying a subject having a disorder affected by modulation of activity of a DUB and administering to the subject a compound as disclosed herein.

In various cases, the methods provided herein are prophylactic methods, and a compound or composition as disclosed herein is administered prior to onset of a disorder. In certain cases, the method further comprises identifying a subject at risk of contracting a disorder associated with DUB activity and/or affected by DUB modulation (e.g., a virus, bacterium, and/or parasite as disclosed herein), and administering an effective amount of a compound as disclosed herein.

In some cases, provided herein are methods of inhibiting proliferation of a cell comprising contacting the cell with an effective amount of a compound as disclosed herein to inhibit proliferation. In some cases, the cell is a cancer cell. Cancer cells contemplated are described elsewhere herein. In various cases, the compound inhibits a DUB endogenous to the cell and inhibits proliferation. In some cases, provided herein are methods of inhibiting Usp9x. In various cases, provided herein are methods of inhibiting Usp5.

In some cases, provided herein are methods of treating neuropathic or inflammatory pain comprising contacting a cell with a compound disclosed herein in an amount sufficient to reduce or alleviate the pain, or to inhibit Usp5 in the cell. In some cases, the contacting comprises administering the compound to a subject suffering from neuropathic or inflammatory pain.

In some cases, the methods disclosed herein further comprises administering a second therapeutic agent. The second therapeutic agent can be administered at the same time as the compound as disclosed herein, or at a different time (e.g., separated by a time period of about 1 hour to about 12 hours). In cases where the agents are administered at the same time, the agents can be co-formulated, or formulated in separate formulations but given at the same time or within about 30 minutes of each other. Contemplated second agents include, e.g., an antiviral, antiparasitic, antibacterial, anticancer agent, agent that treats one or more symptoms of a genetic disorder, and/or an agent that treats a neurodegenerative disorder.

Cancer

Cancer is a disease of the genome characterized by a diverse mutational landscape and genomic alterations that give rise to mutations that lead to abnormal cell transduction cascades. Signal transduction cascades relay growth signals from the cell membrane into the nucleus to initiate transcriptional responses or post-translational protein modifications. Dysregulation of signal transduction cascades in cancer ultimately results in increased cell survival and abnormal cell proliferation. Signal transduction cascades can be regulated by phosphorylation that controls protein function, and ubiquitination that regulates protein turnover and degradation.

Phosphorylation or kinase signaling cascades and the proteasome, a protein complex involved in ubiquitin mediated protein degradation, are major targets in cancer therapy. The anticancer activity of kinase and proteasome inhibitors arise from the disruption of multiple signaling pathways that support the growth, proliferation, and survival of malignant cells.

In addition to chemotherapy and autologous stem-cell transplantation, current therapy for hematologic (B cell) cancers such as multiple myeloma (MM), mantle cell lymphoma (MCL) and chronic myeloid leukemia include the use of proteasome inhibitors (bortezomib, carfilzomib), immunomodulatory drugs (thalidomide, lenalidomide, pomalidomide) and inhibitors of kinase signal transduction cascades involved in B cell signaling (Btk, mTOR inhibitors). Although current treatment strategies for MM and MCL have improved management and overall survival of patients, the diseases remain incurable with a significant number of patients that eventually relapse and succumb to these diseases and emphasizing the need for more effective therapies.

Ubiquitin/proteasome-mediated protein degradation is one of the major mechanisms used by cells for protein turnover or degradation. It involves two successive steps: 1) the attachment of ubiquitin 76 amino acid polypeptide, to a protein substrate mediated by the ubiquitin activating, conjugating and ligating enzymes E1, E2, and E3, and 2) the degradation of the tagged or poly-ubiquitinylated protein by the 26s proteasome complex or lysosome. (Oncogene (2012) 31, 2373-2388 and Acta Pharmacol Sin 2007 September; 28 (9): 1325-1330)

Ubiquitylation is a reversible process where ubiquitin can be removed from ubiquitinylated proteins by an enzymatic reaction catalyzed by deubiquitinases (DUB). Deubiquitinating enzymes are known to have important roles in the regulation of protein stability, proofreading of protein ubiquitination, recycling of ubiquitin and, maintaining free ubiquitin concentrations. DUBs can enhance protein stability by preventing protein degradation.

Consistent with the role of ubiquitination and DUBs in protein turnover and stability, dysregulation in the activity and expression of these enzymes have been linked to cancer development and progression. Due to their role in stabilizing the expression of oncogenic or tumor suppressor proteins, DUBs have been a focus of attention as drug targets or as diagnostic and prognostic biomarkers in oncology research. Several mutated DUBs have been found to act as oncogenes or tumor suppressors, and changes in the expression levels of DUBs were found in several hematologic and malignant solid tumors (lung, pancreas, prostate, colon, thyroid and breast). (Annu Rev Biochem. 2009; 78:363-97)

The DUB Usp9x has recently received considerable attention as potential therapeutic target in several B cell malignancies (MM, MCL, chronic myeloid leukemia) based on the ability of Usp9x to associate and stabilize the expression of the oncogenic protein Myeloid cell leukemia-1 (Mcl-1). (Nature. 2010 Jan. 7; 463(7277):103-7) The Mcl-1 protein is known to promote tumor growth and survival by inhibiting apoptotic or cell death pathways. Mcl-1 is overexpressed in MM, MCL and chronic myeloid leukemia. The Mcl-1 gene was found to be amplified in 10.9% of cancers across multiple tissue types including breast, lung, skin (melanoma), neural tissue and sarcoma. (Nature. 2010 Feb. 18; 463(7283):899-905)

In MM, protein expression levels of Mcl-1 correlate with resistance to chemotherapy, disease relapse and poor survival. Similarly, high expression levels of Usp9x were also found in MCL and MM which may be an underlying mechanism of increased Mcl-1 stability in these diseases. In support of this, knocking down Usp9x expression in MM and MCL cells reduced Mcl-1 levels, reduced MM cell survival and blocked cell proliferation. (Leukemia. 2005 July; 19(7):1248-52)

Mutations in Usp9x gene and high Usp9x protein expression were also found in colorectal, breast, lung ovarian and non-small cell lung carcinoma. Inhibiting expression of Usp9x in MM and colorectal cancer increased cell death, blocked cell proliferation and sensitized cells to chemotherapy suggesting an important role of Usp9x in cancer pathology. (Cancer Biol Ther. 2012 November; 13(13): 1319-24)

High Usp9x protein expression was also found to be elevated in colorectal, breast, lung ovarian and non-small cell lung carcinoma. (Acta Pharmacol. Sin 2007 28(9): 1325-1330). Inhibiting expression of Usp9x in MM and colorectal cancer increased cell death, blocked cell proliferation and sensitized cells to chemotherapy suggesting an important role of Usp9x in cancer pathology. (Nature, 2010, 463(7283):899-905 and Cancer Biol. Ther, 2012 13(13): 1319-24).

A DUB inhibitor WP1130 (see, e.g., WO 08/05954) selectively targets Usp9x, Usp14, Usp5 and UCH37. WP1130 decreased Mcl-1 levels, increased expression of tumor suppressor p53, increased cell death (apoptosis) and blocked cell proliferation in MM and MCL cell lines and patient samples. However, the compound had poor solubility and pharmacokinetic properties, and was not further developed for clinical applications.

To improve the chances of finding clinical leads, a series of chemical modifications were initiated to increase our structure activity relationship (SAR) analysis of inhibitors. To allow a moderate throughput quantitative analysis of potential Usp9x inhibitory compounds, the catalytic domain of Usp9x (Usp9xCD) represented by DNA corresponding to amino acids 1553-1960 of human Usp9x was synthesized using codons optimized for protein expression in E. coli (Genscript). Two compounds, G9 and 067, were identified that had reduced toxicity and improved solubility, potency, as highly specific Usp9x inhibitors. G9 also inhibited the DUB Usp24 that interacts with Usp9x and Mcl-1 and also functions in promoting Mcl-1 stability in MM and MCL cells.

Interestingly, Usp9x and Usp5 were also found to be overexpressed in melanoma cells and in melanoma patients. The use of G9 in melanoma cell lines resulted in the increased expression of the tumor suppressor p53, reduction in Mcl-1 protein, increased cell death, suppression of tumor cell invasiveness, and inhibition of cell proliferation. The compound also enhanced and further increased the apoptotic and anti-cell proliferation effect of the kinase inhibitor vemurafenib that is currently used in ~60% of melanoma patients that harbor a mutation in BRAF, a component of kinase signaling cascade involved in cell proliferation and survival. In melanoma xenografts, use of G9 monotherapy reduced tumor growth and did not have any notable side effects in animal weight, behavior and mobility.

The improved solubility, pharmacokinetoic properties and reduced toxicity suggests that two identified Usp9x inhibitors may be used as therapeutic agents in multiple cancer types where Mcl-1, Usp9x and Usp24 are amplified or overexpressed.

The methods and compounds disclosed herein are useful in treating cancer, e.g., preventing, inhibiting and/or ameliorating a cancer or symptom of cancer. In some cases, the method of treating the cancer comprises inhibiting of a DUB, e.g., a DUB involved in survival or proliferation of the cancer.

Specific cancers contemplated include, but are not limited to, chronic myelogenous leukemia (CML), melanoma, acute lymphocytic leukemia, chronic lymphocytic leukemia, acute myelogenous leukemia, B-cell lymphoma, mantle cell lymphoma, multiple myeloma, plasma cell dyscrasia, myeloproliferative disorders, glioblastoma, Kaposi's sarcoma, and nasopharyngeal carcinoma (EBV). Other cancers contemplated include lung cancer, colon cancer, pancreatic cancer, breast cancer, prostate cancer, melanoma, and solid tumors.

Neuropathic or Inflammatory Pain

It has been found that Usp5 is modulates neuropathic and inflammatory pain by enhancing $Ca_v3.2$ channel activity (see Garcia-Caballero et al., Neuron, 83:1144-1158 (2014)). Thus, provided herein are methods of treating or alleviating neuropathic or inflammatory pain by administering a compound as disclosed herein in an amount sufficient to inhibit Usp5.

Pathogenic Infections

The methods and compounds disclosed herein are useful in treating pathogenic infections, e.g., preventing, inhibiting and/or ameliorating a pathogenic infection or symptom of a pathogenic infection. In some cases, the methods and compounds disclosed herein are useful in treating a condition due to a pathogenic infection.

Intentional contamination of the food and water supplies represents a major threat to the health and health-related services in the US population as a whole and to our armed forces serving throughout the world. Many of the category B water- and food-borne pathogens have specific properties, e.g. low infectious dose, high stability, that make them attractive candidates for this type of bioterrorism. To thwart this potential threat, methods or agents that provide protection or prophylaxis against these defined pathogens are urgently needed. Ideally, agents that provide protection against a wide spectrum of threats would be desirable. The compounds disclosed herein have broad activity against multiple pathogens. For example, G9 is a potent inhibitor of diverse category A and B pathogens, and related family members, e.g., murine norovirus, Tulane virus, *Listeria monocytogenes* and *Toxoplasma gondii* infection as well as Norwalk virus replication. In addition, it also has antiviral activity against Sindbis virus and La Crosse virus. In certain cells the compounds disclosed herein inhibit a deubiquitinase and this action results in accumulation of ubiquitinated proteins in the cytoplasmic and aggresomal compartment of the cell. This can establish an inhospitable environment for pathogen infection or replication within the target cell. Thus, these compounds are used as an antimicrobial inhibitor that can effectively suppress multiple pathogens. The compounds disclosed herein block the infectivity of category A and/or B pathogens, and/or related family members.

Contemplated are pathogens that use a DUB in their infection mechanism. In some cases, the pathogen uses a DUB endogenous to the infected cell. In various cases, the pathogen uses a DUB endogenous to the pathogen.

Contemplated diseases or disorders due to a pathogenic infection include gastroenteritis, encephalitis, respiratory tract infections (e.g., SARS), virus-induced cancers, rabies, hemorrhagic fevers (e.g., Crimean-Congo, Dengue), Rift valley fever, listeriosis, or toxoplasmosis. Also contemplated diseases or disorders due to a pathogenic infection include meningitis, myocarditis, hepatitis, bacterimia, and skin infections.

Contemplated pathogens include viral, bacterial, fungal, and parasitic pathogens. Contemplated pathogenic viruses include a calicivirus (e.g., norovirus, sapovirus), a picornavirus, a Togavirus, a Bunyavirus, a Rhabdovirus, a herpes virus, an adenovirus, an arterivirus, a coronavirus, a flavivirus, a paramyxovirus, a papillomavirus, a virus encoding for an ovarian tumor (OTU)-like protease, a baculovirus, or a nairovirus. Other contemplated pathogenic viruses include polyoma viruses and retroviruses.

Specific viruses contemplated include encephalomyocarditis virus (EMCV), Sindbis virus (SiNV), La Crosse virus (LaCV), Norwalk virus, Tulane virus, rotavirus, Epstein-Barr (EBV), herpesvirus, Dengue virus, and papillomavirus. Further specific viruses contemplated include cytomegalovirus, BK virus, hepatitis C virus, and HIV.

Contemplated bacteria include *Chlamydia*, *Escherichia*, *Salmonella*, *Yersinia*, *Burkholderia*, *Haemophilus*, *Listeria*, and *Mycobacterium*. Other bacteria contemplated include *Staphylococcus aureus*, or more specifically methicillin-resistent *Staph aureus* (MRSA).

Contemplated parasites or fungi include *Plasmodium falciparum*, *Toxoplasma gondii*, *Entamoeba histolytica*, *Giardia lamblia*, *Trypanosoma brucei*, *Trypanosoma cruzi*, *Cestoda*, *Clonorchis*, *Opisthorchis*, *Strongylocides*, *Candida*, *Aspergillus*, and *Cryptococcus*.

Dosing and Pharmaceutical Formulations

The terms "therapeutically effective amount" and "prophylactically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, reduction in symptoms, or by any of the assays or clinical diagnostic tests described herein. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

Dosages of the therapeutic can alternately be administered as a dose measured in mg/kg. Contemplated mg/kg doses of the disclosed therapeutics include about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg.

As herein, the compounds described herein may be formulated in pharmaceutical compositions with a pharmaceutically acceptable excipient, carrier, or diluent. The compound or composition comprising the compound is administered by any route that permits treatment of the disease or condition. One route of administration is oral administration. Additionally, the compound or composition comprising the compound may be delivered to a patient using any standard route of administration, including parenterally, such as intravenously, intraperitoneally, intrapulmonary, subcutaneously or intramuscularly, intrathecally, topically, transdermally, rectally, orally, nasally or by inhalation. Slow release formulations may also be prepared from the agents described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers.

Controlled release formulations are also obtained through encapsulation of dispersed micro-particles or emulsified micro-droplets via known dispersion or emulsion coating technologies.

Administration may take the form of single dose administration, or a compound as disclosed herein can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

In an embodiment, the pharmaceutical compositions are formulated with one or more pharmaceutically acceptable excipient, such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents.

Formulations, e.g., for parenteral or oral administration, are most typically solids, liquid solutions, emulsions or suspensions, while inhalable formulations for pulmonary administration are generally liquids or powders. A pharmaceutical composition can also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

The pharmaceutical compositions described herein are formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). The suspensions may also contain one or more preservatives (e.g., acetic acid, methyl or n-propyl p-hydroxy-benzoate); one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using those suitable dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compounds described herein may be formulated for oral administration in a lipid-based formulation suitable for low solubility compounds. Lipid-based formulations can generally enhance the oral bioavailability of such compounds.

As such, pharmaceutical compositions comprise a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In some embodiments, cyclodextrins may be added as aqueous solubility enhancers. Exemplary cyclodextrins include hydroxypropyl, hydroxyethyl, glucosyl, maltosyl and maltotriosyl derivatives of α-, β-, and γ-cyclodextrin. A specific cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the invention in the composition.

Combination Therapy

The methods of the embodiments also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In some cases, a compound disclosed herein is administered and/or formulated with a second therapeutic—e.g., a chemotherapeutic.

Chemotherapeutic agents contemplated for use include, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; non-steroidal antiandrogens such as flutamide; kinase inhibitors, histone deacetylase inhibitors, methylation inhibitors, proteasome inhibitors, monoclonal antibodies, oxidants, anti-oxidants, telomerase inhibitors, BH3 mimetics, ubiquitin ligase inhibitors, Stat inhibitors, and nanoparticles.

The invention will be more fully understood by reference to the following examples which detail exemplary embodiments of the invention. They should not, however, be construed as limiting the scope of the invention. All citations throughout the disclosure are hereby expressly incorporated by reference.

EXAMPLES

Synthesis of Compounds

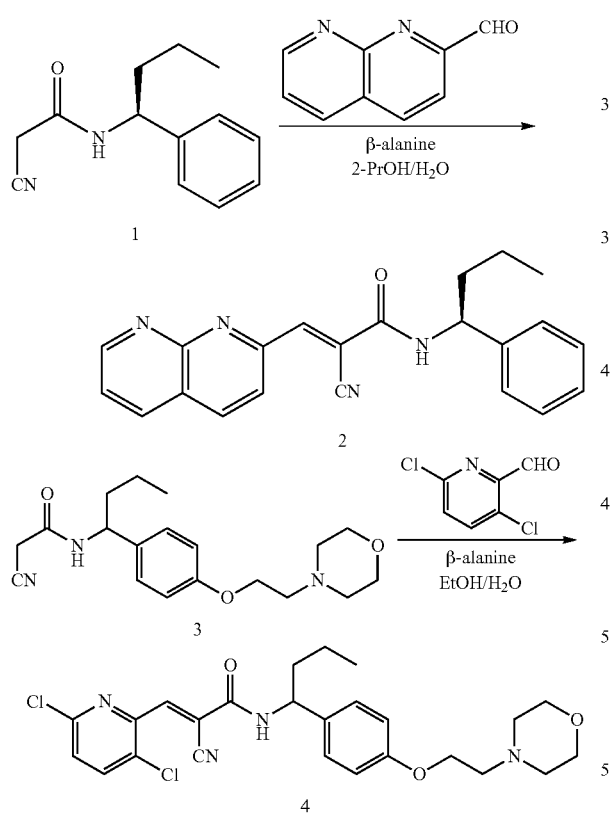

(S,E)-2-Cyano-3-(1,8-naphthyridin-2-yl)-N-(1-phenylbutyl)acrylamide (2). A solution of 1,8-naphthyridine-2-carbaldehyde (73.1 mg, 0.46 mmol), (S)-2-cyano-N-(1-phenylbutyl)acetamide (Donato N J, Wobus C, Showalter H D H, Talpaz M, Perry J W, Sorenson R J, O'Riordan M X D, Jin Y. Deubiquitinase Inhibitors and Methods for Use of the Same. WO 2012040527; 1; 50 mg, 0.23 mmol), β-alanine (165 mg, 1.85 mmol), 2-propanol (6 mL) and water (3 mL). was stirred under nitrogen at room temperature for 18 h. The mixture was diluted with water and extracted with ethyl acetate. The combined extracts were washed twice with water, saturated brine, dried over sodium sulfate and concentrated to leave a yellow film. Purification by preparative thick layer chromatography, eluting with 1.5% methanol in dichloromethane provided 2 (34.1 mg, 41%) as a yellow foam: $^1$H NMR (500 MHz, chloroform-d) δ 9.25 (d, J=4.2 Hz, 1H), 8.53 (s, 1H), 8.34 (d, J=8.3 Hz, 1H), 8.25 (d, J=8.1 Hz, 1H), 7.91 (d, J=8.3 Hz, 1H), 7.58 (dd, J=8.2, 4.2 Hz, 1H), 7.38-7.25 (m, 5H), 6.85 (d, J=8.1 Hz, 1H), 5.11 (q, J=7.7 Hz, 1H), 1.99-1.83 (m, 2H), 1.38 (m, 2H), 0.97 (t, J=7.3 Hz, 3H); MS (ES) m/z 357.3 (M+H)$^+$.

(E)-2-Cyano-3-(3,6-dichloropyridin-2-yl)-N-(1-(4-(2-morpholinoethoxy)phenyl)butyl)acrylamide (4). This compound was synthesized from 3,6-dichloropicolinaldehyde and 2-cyano-N-(1-(4-(2-morpholinoethoxy)phenyl)butyl)acetamide (3; Donato N J, Wobus C, Showalter H D H, Talpaz M, Perry J W, Sorenson R J, O'Riordan M X D, Jin Y. Deubiquitinase Inhibitors and Methods for Use of the Same. WO 2012040527), β-alanine, and aqueous ethanol by the previously described generalized procedure (Donato N J, Wobus C, Showalter H D H, Talpaz M, Perry J W, Sorenson R J, O'Riordan M X D, Jin Y. Deubiquitinase Inhibitors and Methods for Use of the Same. WO 2012040527): $^1$H NMR (400 MHz, chloroform-d) δ 8.61 (s, 1H), 7.74 (d, J=8.5 Hz, 1H), 7.38 (d, J=8.5 Hz, 1H), 7.24 (d, 2H), 6.89 (d, J=8.7 Hz, 2H), 6.78 (d, J=7.8 Hz, 1H), 5.01 (q, J=7.6 Hz, 1H), 4.10 (t, J=5.7 Hz, 2H), 3.78-3.71 (m, 4H), 2.80 (t, J=5.7 Hz, 2H), 2.60-2.55 (m, 4H), 1.96-1.76 (m, 2H), 1.41-1.30 (m, 2H), 0.95 (t, J=7.4 Hz, 3H); MS (ES) m/z 501.3 (M−H$^+$/503.4 (M−H)$^+$ (3:1 Cl isotope pattern).

Additional compounds were made in a similar manner.

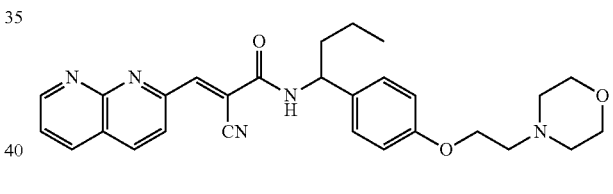

(E)-2-Cyano-N-(1-(4-(2-morpholinoethoxy)phenyl)butyl)-3-(1,8-naphthyridin-2-yl)acrylamide. The title compound was synthesized by using a procedure similar to that described for the preparation of compound 4. The crude material was purified with 3% 2-propanol in dichloromethane to give the title compound (2.9 mg, 41%) as a yellow film: $^1$H NMR (500 MHz, chloroform-d) δ 9.26 (d, J=4.1 Hz, 1H), 8.53 (s, 1H), 8.35 (d, J=8.3 Hz, 1H), 8.25 (d, J=8.0 Hz, 1H), 7.91 (d, J=8.3 Hz, 1H), 7.59 (dd, J=8.2, 4.2 Hz, 1H), 7.28 (d, J=8.0 Hz, 3H), 6.91 (d, J=8.4 Hz, 2H), 6.77 (d, J=8.1 Hz, 1H), 5.06 (q, J=7.7 Hz, 1H), 4.12 (t, J=5.7 Hz, 2H), 3.74 (t, J=4.6 Hz, 4H), 2.81 (t, J=5.7 Hz, 2H), 2.63-2.54 (m, 4H), 1.89 (m, 2H), 1.36 (m, 2H), 0.96 (t, J=7.4 Hz, 3H); MS (ES$^+$) m/z 486.1 (M+H)$^+$.

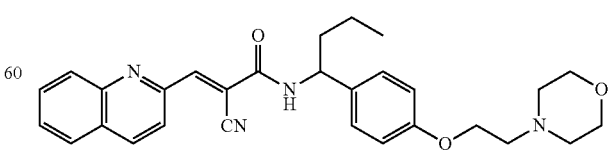

(E)-2-Cyano-N-(1-(4-(2-morpholinoethoxy)phenyl)butyl)-3-(quinolin-2-yl)acrylamide. The title compound was synthesized by using a procedure similar to that described for the preparation of compound 4. The crude material was purified with 3% methanol in dichloromethane to give the title compound (8.6 mg, 61%) as a yellow film: $^1$H NMR (500 MHz, chloroform-d) δ 8.45 (s, 1H), 8.25 (dd, J=13.8, 8.5 Hz, 2H), 7.85 (d, J=8.2 Hz, 1H), 7.79 (t, J=7.6 Hz, 1H), 7.69 (d, J=8.4 Hz, 1H), 7.64 (t, J=7.5 Hz, 1H), 7.28 (d, J=8.3 Hz, 2H), 6.90 (d, J=8.4 Hz, 2H), 6.77 (d, J=8.0 Hz, 1H), 5.06 (q, J=7.7 Hz, 1H), 4.26 (br s, 2H), 3.86 (br s, 4H), 2.99 (br s, 2H), 2.78 (br s, 2H), 1.89 (m, 2H), 1.37 (m, 2H), 0.97 (t, J=7.3 Hz, 3H); MS (ES$^+$) m/z 485.3 (M+H)$^+$.

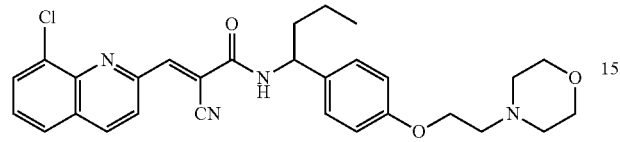

(E)-3-(8-Chloroquinolin-2-yl)-2-cyano-N-(1-(4-(2-morpholinoethoxy)phenyl)butyl)-acrylamide. The title compound was synthesized by using a procedure similar to that described for the preparation of compound 4. The crude material was purified with 3% methanol in dichloromethane to give the title compound (4.7 mg, 31%) as a yellow film: $^1$H NMR (500 MHz, chloroform-d) δ 8.47 (s, 1H), 8.30 (d, J=8.3 Hz, 1H), 7.93 (d, J=7.4 Hz, 1H), 7.78 (d, J=8.2 Hz, 1H), 7.72 (d, J=8.4 Hz, 1H), 7.55 (t, J=7.8 Hz, 1H), 7.28 (d, J=8.3 Hz, 2H), 6.90 (d, J=8.4 Hz, 2H), 6.84 (d, J=8.1 Hz, 1H), 5.06 (q, J=7.6 Hz, 1H), 4.12 (t, J=5.6 Hz, 2H), 3.74 (t, J=4.6 Hz, 4H), 2.82 (d, J=6.8 Hz, 2H), 2.58 (d, J=5.1 Hz, 4H), 1.89 (m, 2H), 1.37 (m, 2H), 0.97 (t, J=7.3 Hz, 3H); MS (ES$^+$) m/z 519.2 (M+H)$^+$.

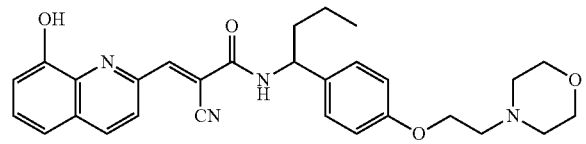 [SMILES: CCCC(NC(=O)/C(C#N)=C/c1ccc2cccc(O)c2n1)c1ccc(OCCN2CCOCC2)cc1]

(E)-2-Cyano-3-(8-hydroxyquinolin-2-yl)-N-(1-(4-(2-morpholinoethoxy)phenyl)butyl)-acrylamide. The title compound was synthesized by using a procedure similar to that described for the preparation of compound 4. The crude material was purified with 3% methanol in dichloromethane to give the title compound (6.1 mg, 42%) as a yellow film: $^1$H NMR (500 MHz, chloroform-d) δ 8.42 (s, 1H), 8.27 (d, J=8.4 Hz, 1H), 8.15 (s, 1H), 7.59 (m, 2H), 7.38 (d, J=8.2 Hz, 1H), 7.29 (d, J=8.4 Hz, 2H), 6.91 (d, J=8.3 Hz, 2H), 6.74 (d, J=8.0 Hz, 1H), 5.06 (q, J=7.6 Hz, 1H), 4.12 (t, J=5.7 Hz, 2H), 3.74 (t, J=4.6 Hz, 4H), 2.81 (t, J=5.8 Hz, 2H), 2.58 (t, J=4.7 Hz, 4H), 1.89 (m, 3H), 1.37 (m, 3H), 0.97 (t, J=7.3 Hz, 3H); MS (ES$^+$) m/z 501.3 (M+H)$^+$.

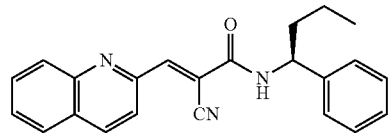 [SMILES: CCC[C@H](NC(=O)/C(C#N)=C/c1ccc2ccccc2n1)c1ccccc1]

(S,E)-2-Cyano-N-(1-phenylbutyl)-3-(quinolin-2-yl)acrylamide. The title compound was synthesized by using a procedure similar to that described for the preparation of compound 2. The crude material was purified with 10% ethyl acetate/hexanes to give the title compound (4.1 mg, 42%) as a colorless film: $^1$H NMR (500 MHz, chloroform-d) δ 8.46 (s, 1H), 8.25 (dd, J=11.0, 8.4 Hz, 2H), 7.86 (d, J=8.2 Hz, 1H), 7.80 (t, J=7.7 Hz, 1H), 7.70 (d, J=8.3 Hz, 1H), 7.64 (t, J=7.5 Hz, 1H), 7.37 (m, 4H), 7.30 (t, J=6.8 Hz, 1H), 6.83 (d, J=8.2 Hz, 1H), 5.12 (q, J=7.6 Hz, 1H), 1.91 (m, 2H), 1.38 (m, 2H), 0.98 (t, J=7.3 Hz, 3H); MS (ES$^+$) m/z 356.2 (M+H)$^+$.

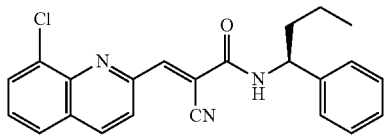 [SMILES: CCC[C@H](NC(=O)/C(C#N)=C/c1ccc2cccc(Cl)c2n1)c1ccccc1]

(S,E)-3-(8-Chloroquinolin-2-yl)-2-cyano-N-(1-phenylbutyl)acrylamide. The title compound was synthesized by using a procedure similar to that described for the preparation of compound 2. The crude material was purified with 20% ethyl acetate/hexanes to give the title compound (3.5 mg, 32%) as a colorless film: $^1$H NMR (500 MHz, chloroform-d) δ 8.47 (s, 1H), 8.30 (d, J=8.3 Hz, 1H), 7.93 (d, J=7.4 Hz, 1H), 7.78 (d, J=8.1 Hz, 1H), 7.72 (d, J=8.4 Hz, 1H), 7.56 (t, J=7.9 Hz, 1H), 7.37 (m, 4H), 7.30 (m, 1H), 6.91 (d, J=8.1 Hz, 1H), 5.12 (q, J=7.6 Hz, 1H), 1.91 (m, 2H), 1.40 (m, 2H), 0.98 (t, J=7.3 Hz, 3H); MS (ES$^+$) m/z 390.2 (M+H)$^+$.

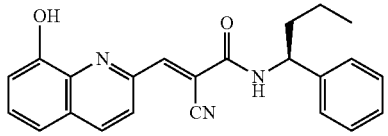 [SMILES: CCC[C@H](NC(=O)/C(C#N)=C/c1ccc2cccc(O)c2n1)c1ccccc1]

(S,E)-2-Cyano-3-(8-hydroxyquinolin-2-yl)-N-(1-phenylbutyl)acrylamide. The title compound was synthesized by using a procedure similar to that described for the preparation of compound 2. The crude material was purified with 20% ethyl acetate/hexanes to give the titled compound (8.4 mg, 82%) as a yellow film: $^1$H NMR (500 MHz, chloroform-d) δ 8.43 (s, 1H), 8.28 (d, J=8.4 Hz, 1H), 8.16 (s, 1H), 7.59 (m, 2H), 7.38 (m, 4H), 7.29 (m, 1H), 6.80 (d, J=8.0 Hz, 1H), 5.12 (q, J=7.6 Hz, 1H), 1.92 (m, 2H), 1.40 (m, 2H), 0.98 (t, J=7.3 Hz, 3H); MS (ES$^+$) m/z 372.2 (M+H)$^+$.

Assessing Compounds for Activity Against DUB

Compounds are screened for DUB inhibitory and apoptotic activity in a panel of CML, myeloma and Mantle cell lymphoma cell lines. Selected compounds are also tested for DUB inhibition in intact cells and in isolated DUB (Usp9x-UCH domain) enzyme preparations. General descriptions of the methods employed in these assays can be found, e.g., in Kapuria, et al., A novel small molecule deubiquitinase inhibitor blocks Jak2 signaling through Jak2 ubiquitination, *Cell Signal*, 2011, 23(12):2076-85; Kapuria, et al., Deubiquitinase inhibition by small-molecule WP 1130 triggers aggresome formation and tumor cell apoptosis. *Cancer Res*, 2010. 70(22): p. 9265-76; Sun, et al., Bcr-Abl ubiquitination and Usp9x inhibition block kinase signaling and promote CML cell apoptosis. *Blood*, 2011. 117(11): p. 3151-62; Kapuria, et al., Protein cross-linking as a novel mechanism of action of a ubiquitin-activating enzyme inhibitor with anti-tumor activity. *Biochem Pharmacol*, 2011. 82(4): p. 341-9; and Bartholomeusz, et al., Activation of a novel Bcr/Abl destruction pathway by WP1130 induces apoptosis of chronic myelogenous leukemia cells. *Blood,* 2007. 109 (8): p. 3470-8.

A series of chemical modifications were initiated to increase our structure activity relationship (SAR) analysis of inhibitors. To allow a moderate throughput quantitative analysis of potential Usp9x inhibitory compounds, the catalytic domain of Usp9x (Usp9xCD) represented by DNA corresponding to amino acids 1553-1960 of human Usp9x was synthesized using codons optimized for protein expression in *E. coli* (Genscript). The DNA was cloned into a ULP1-protease cleavable N-terminal His6-Smt3-fusion tag expression vector, derived from pET-28. Protein expression was induced at OD600 2.0, in TB media with Kanamycin overnight at 16° C. Cells were harvested and flash frozen before use. Purification involved a Ni-NTA affinity column, followed by protease-cleavage to remove the affinity tag, passage through a second Ni-NTA column to remove the protease and fusion-tag, and then a final S-200 column equilibrated with 100 mM KCl, 20 mM HEPES, pH 7.4, 2 mM DTT. Protein was concentrated to roughly 20-40 mg/ml before aliquots were flash-frozen. All steps were performed in the presence of reducing agents, either BME, DTT, or TCEP.

Purified recombinant enzyme in buffer containing 2 mM DTT was buffer exchanged into 25 mM Tris-HCl, 50 mM NaCl and 1 mg/ml BSA using a spin column. Three hundred nM of Usp9xCD was incubated with an indicated final concentration of inhibitor for 30 min at 37° C. before the addition of 1.5 µM Ub-AMC (BostonBiochem) in a final reaction volume of 25 µl. Fluorescence was monitored (Ex 380 nm, Em 460 nm) in a 384 well plate and read over time in a Molecular Devices SPECTRA MAX M2 plate reader (heated to 37° C.). $IC_{50}$ values were estimated by integrating the slope of each reaction using GraphPad 6.

Two hundred and ten (210) novel chemical structures were screened for Usp9xCD inhibitory activity using this assay. Of those 210 structures, two compounds (G9, 067) emerged as superior inhibitors of Usp9xCD (compared to WP1130). Fluorescent scans were used to assess Usp9xCD inhibitory activity in this enzyme assay for all compounds of interest. Each assay was performed in duplicate and the linear region of each reaction curve was used to calculate $IC_{50}$ values for Usp9xCD inhibition which are tabulated in Table 1.

TABLE 1

| Compound | IC50 for Usp9X |
|---|---|
| WP 1130 | 4.8 µM |
| 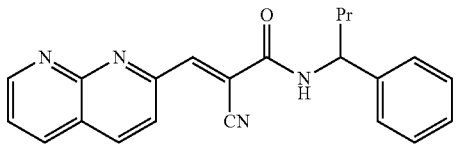 (067) | 1.2 µM |
| 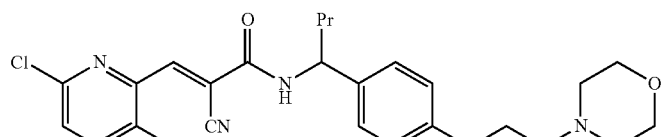 (G9) | 1.6 µM |
| 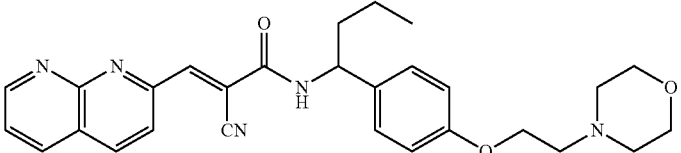 | 6.23 µM |
| 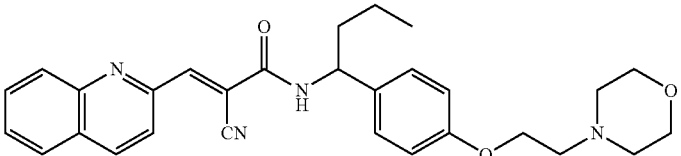 | 5.97 µM |
| 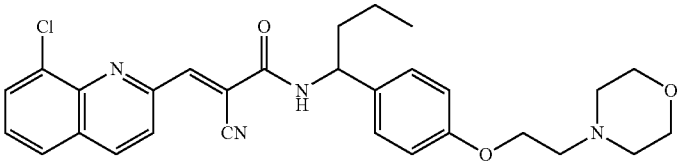 [SMILES: CCCC(NC(=O)/C(C#N)=C/c1ccc2cccc(Cl)c2n1)c1ccc(OCCN2CCOCC2)cc1] | 10.73 µM |

TABLE 1-continued

| Compound | IC50 for Usp9X |
|---|---|
| [Structure: 8-hydroxyquinoline-CH=C(CN)-C(O)NH-CH(propyl)-phenyl-O-CH2CH2-morpholine] | 5.12 μM |
| [Structure: quinoline-CH=C(CN)-C(O)NH-CH(propyl)-phenyl] | 4.61 μM |
| [Structure: 8-chloroquinoline-CH=C(CN)-C(O)NH-CH(propyl)-phenyl] | 1.99 μM |
| [Structure: 8-hydroxyquinoline-CH=C(CN)-C(O)NH-CH(propyl)-phenyl] | 6.13 μM |

To determine whether the compounds also inhibit Usp9x in intact cells, DUB activity was measured in control and treated cells as previously described. In brief, control and treated cells were lysed by sonication in DUB assay buffer [50 mM Tris-HCl (pH 7.5), 5 mM $MgCl_2$, 250 mM sucrose, 1 mM PMSF, 1× Roche proteinase inhibitory cocktail] and 20 μg of protein from the supernatant fraction (after a 14,000×g spin) were incubated with 200 nM HA-Ub vinyl-sulfone (Boston Biochem) in a final volume of 20 μl. After 90 min at 37° C., reactions were stopped with the addition of 5×-sample buffer. DUB activity was detected by SDS-PAGE resolution of the protein followed by nitrocellulose membrane transfer and immunoblotting with anti-HA. A dose-response of WP1130, G9 and YJ-8-067 (cells treated with 1.25, 2.5 and 5 μM compound for 4 hours) was performed in Z138 lymphoma cells. The results demonstrate that each compound was able to inhibit Usp9x activity in intact cells and reduce the level of a downstream target of Usp9x, the pro-survival protein Mcl-1. Further investigations were made on the Usp9x inhibitory activity of G9 based on its greater efficacy against Usp9x and increased aqueous solubility when compared to WP1130 (2.6 μM for WP1130 vs. 19.8 μM for G9).

The time required for G9-mediated Usp9x inhibition in intact multiple myeloma (MM1.S) cells and primary tumor cells from a patient with plasma cell leukemia (PCL) was investigated. MM1.ST (FIG. 1, left) or PCL (FIG. 1, right) cells were treated with 5 μM of compound for the time indicated before Usp9x activity was assessed as described above. The results indicate that as little as 5 minutes of G9 treatment was able to inhibit Usp9x activity by >80% and 60 minute to achieve 100% Usp9x inhibition in either tumor sample. G9-mediated Usp9x inhibition was also associated with a reduction in Mcl-1 and the activation of caspase activity as indicated by the cleavage of the caspase substrate PARP. These results demonstrate that G9 rapidly inhibits Usp9x activity in primary tumors and tumor cell lines with impact on Mcl-1 and apoptosis of tumor cells.

Usp9x is highly expressed and activated in melanoma cells. The effect of G9 on Usp9x activity in a representative melanoma cell line, A375, and an A375 variant cell line that is resistant to the BRAF kinase inhibitor, vemurafenib, were examined. Treatment with G9 resulted in inhibition of Usp9x activity in either cell type. G9 is able to inhibit Usp9x activity in hematologic malignancies and some solid tumors.

To determine whether G9 or 067 had anti-tumor activity in animals, we first assessed their properties in mice when introduced intravenously (IV) or by oral gavage (PO). G9 or 067 was administered once to two mice per group at the indicated dosage level and route (IV or PO) and plasma was collected at the time point indicated after administration. Compound concentration in the plasma was measured by high performance liquid chromatography coupled with mass spectroscopy detection (LC/MS).

Balb/c mice were treated with either 067 or G9 dissolved in dimethyl sulfoxide: polyethylene glycol 300 (1:1) and administered as indicated. The level of each compound in the plasma of each mouse at the time point indicated is shown in the line graph. The area under the curve (AUC) was calculated and tabulated below each line graph. The analysis demonstrates that both compounds are bio-available following IV administration, with higher peak levels achievable with G9. Both compounds have poor oral bio-availability and relatively short half-lives. The level of each compound in the plasma of each mouse at the time point indicated is shown Table 2. Several pharmacokinetic parameters were also calculated. The analysis demonstrates that both compounds are bio-available following IV administration, with higher peak levels achievable with G9. Both compounds have poor oral bio-availability and relatively short half-lives (G9 half-life 1.5 to 2 hours; 067 half-life is <1 hour). Compounds were also administered by intraperitoneal (IP) injection and showed similar characteristics as those derived by IV administration (not shown). The half-life of G9 was similar to 067 when administered by IP injection (30-60 min). Based on these assessments, G9 was further evaluated for anti-tumor activity in mice.

TABLE 2

| Sample Time (Hours) | Concentration of 067 in plasma (ng/mL) | | | |
| --- | --- | --- | --- | --- |
| | IV Mouse 1 (5 mg/kg) | IV Mouse 2 (5 mg/kg) | PO Mouse 1 (10 mg/kg) | PO Mouse 2 (10 mg/kg) |
| 0.5 | 397 | 301 | 50.8 | 117 |
| 2 | 99.1 | 79.6 | 10.6 | 40.6 |
| 4 | 63.1 | 33.4 | 13.3 | 30 |
| 7 | 71.4 | 33.7 | 15.9 | 11.4 |
| $AUC_{last}$ (hr · ng/mL) | 992.9 | 691.6 | 126.5 | 280.2 |

| Time (Hours) | Concentration of G9 in plasma (ng/mL) | | | |
| --- | --- | --- | --- | --- |
| | IV1 (10 mg/kg) | IV2 (10 mg/kg) | PO1 (30 mg/kg) | PO2 (30 mg/kg) |
| 0.5 | 1880 | 1220 | 60.8 | 78.7 |
| 2 | 395 | 520 | 35.8 | 59 |
| 4 | 126 | 289 | 44.5 | 57.1 |
| 7 | 38.6 | 208 | 37.6 | 16.1 |
| $AUC_{last}$ (hr · ng/mL) | 3734.7 | 3569.8 | 291 | 348.9 |

Figure 2:
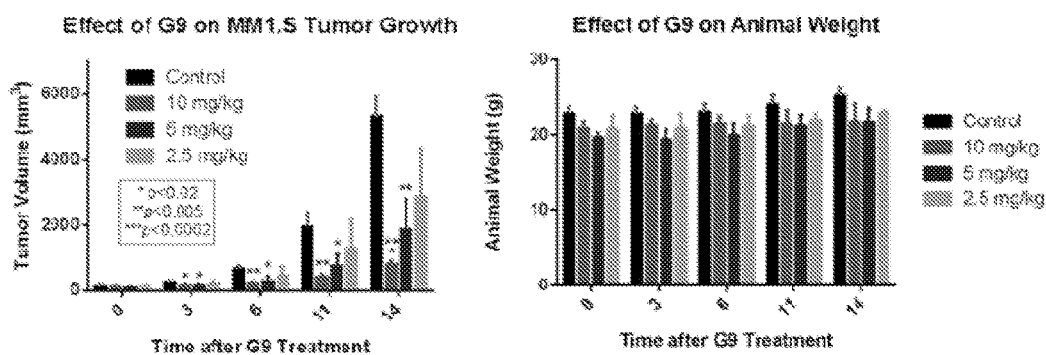
FIG. 2 shows effect of G9 on MM1.S tumor growth and on animal weight at 2.5, 5, and 10 mg/kg doses.

Ten million MM1.S tumor cells were injected into the dorsal region of twenty female NOD/SCID/gamma-2 knockout mice (NSG) weighing ~20 grams each. After 3 weeks tumors became visible and measurable with calipers. Mice were separated into four groups of 5 mice each and IP injected with G9 dissolved in 55% dimethyl sulfoxide, 25% polyethylene glycol 300, 20% phosphate-buffered saline at dose levels of 0, 2.5, 5 and 10 mg/kg mouse body weight. Animals were injected once per day for 14 days and tumor growth (measured with calipers) and animal weight were monitored over the treatment interval. The resulting changes in tumor growth for each group are shown and represented as the average+/−standard error of the mean for each group. The p-values were calculated using GraphPad InStat. P-values lower than 0.05 are considered significant. The results are shown in FIG. 2, which illustrate that all doses of G9 reduced MM1.S tumor growth, which was highly significant compared to control (0 mg/kg G9) mice at G9 doses of 5 and 10 mg/kg. Animal weight was not affected by G9 injection in any of the mice. The results demonstrate that G9 suppresses MM1.S tumor growth in mice. Twenty female NSG mice were inoculated subcutaneously with 10 million MM1.S cells in Matrigel and cell culture media (1:1) in a total volume of 0.1 mL. When tumors were measurable with calibers (3 weeks post tumor cell injection), mice were divided into 4 groups of five mice each and treated with the dose of G9 indicated. Tumor growth (left) and animal weight (right) were recorded at the interval noted. The results represent the average+/−SD of 5 animals per data point. P-values <0.05 are considered significant and were calculated using GraphPad InStat. All G9 doses reduced tumor growth, with 5 and 10 mg/kg doses resulting in a significant reduction in MM1.S tumor growth when compared to controls.

Figure 3:
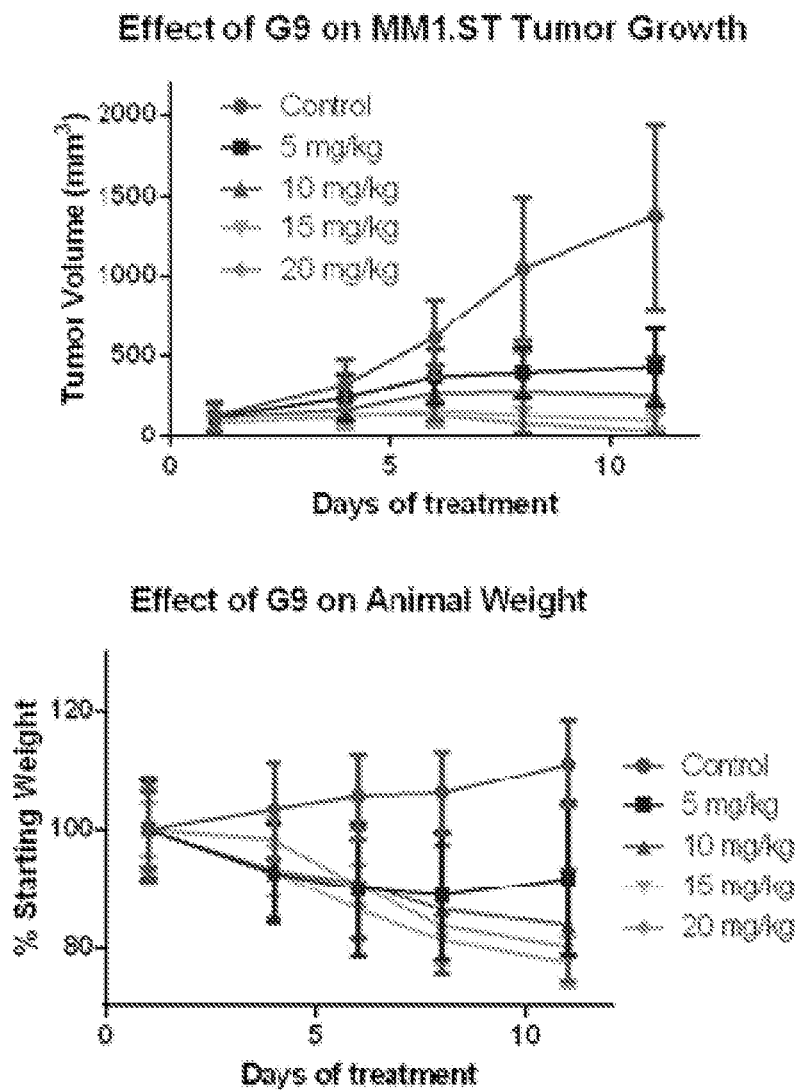
FIG. 3 shows effect of G9 on MM1.S tumor growth and on animal weight at 5, 10, 15, and 20 mg/kg doses.
Figure 4:
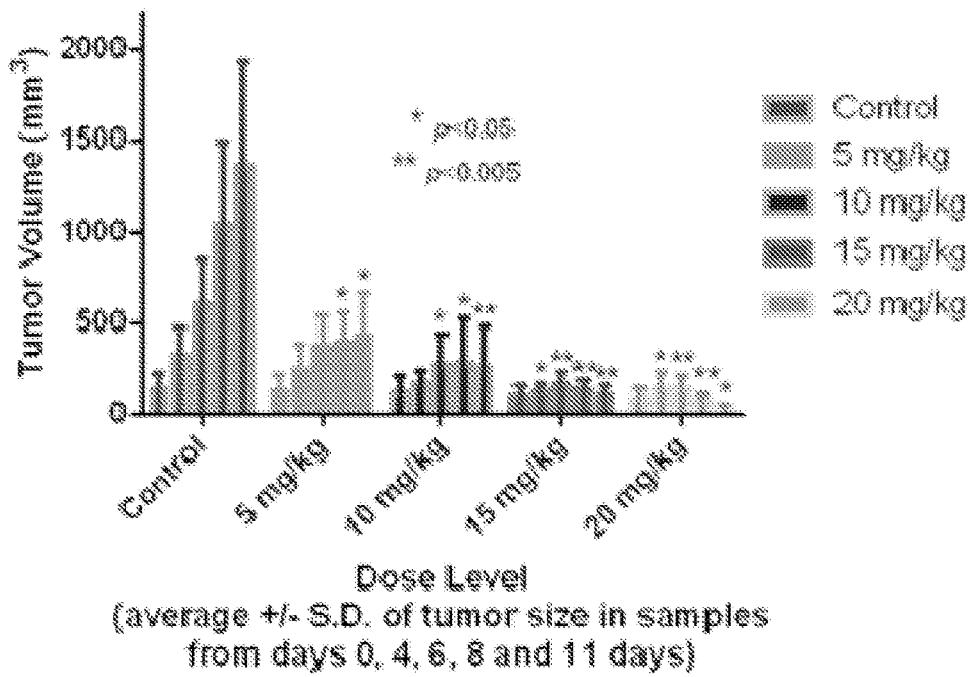
FIG. 4 shows the tumor volumes (top) and extracted tumors from control and treated mice (bottom) from the animal study shown in FIG. 3 are illustrated.
Figure 4:
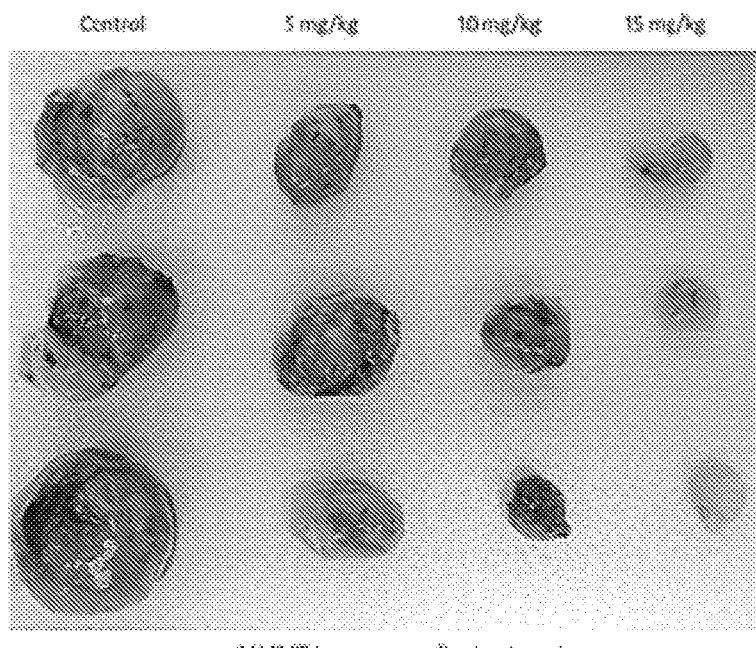
Figure 7:
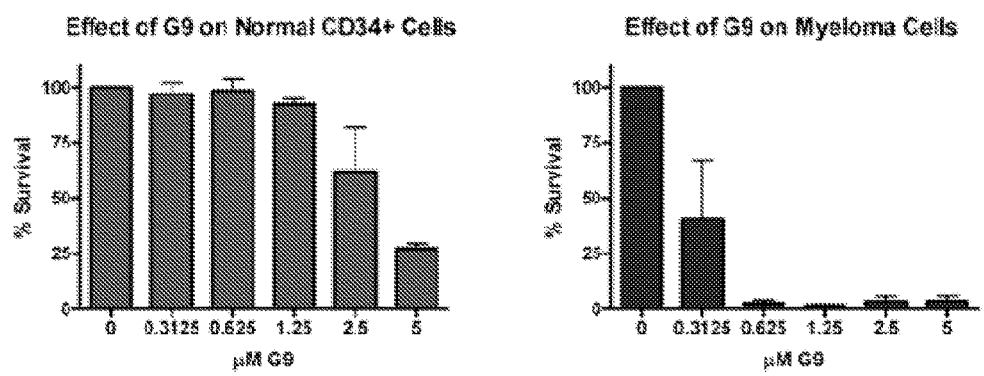
FIG. 7 shows CD34+ cells from normal and myeloma cell lines treated with G9.

A second animal study was conducted in NSG mice with mice receiving higher dose levels of G9. Tumor inoculation and compound administration were similar to those utilized in the lower dose study. However, 3 mice per treatment group were used in this study and additional G9 doses were tested for safety and efficacy. As shown in FIG. 3, all G9 doses suppressed MM1.S tumor growth, with 15 and 20 mg/kg doses resulting in tumor regression. NSG mice were inoculated with MM1.S tumors as described in FIG. 7. When tumors were measurable with calipers, mice were placed into 5 groups of 3 mice each and treated with G9 at 0, 5, 10, 15 and 20 mg/kg for 12 days with daily injection. Tumor size (left) and animal weight (right) were recorded over the treatment interval. Tumor regressions were noted at the 15 and 20 mg/kg doses and doses of 10-20 mg/kg resulted in some weight loss in mice. The result of G9 treatment is also depicted as tumor volume over time for each treatment group (FIG. 4—top). Tumors extracted from each of the three mice in each treatment group following the last injection were photographed and shown in FIG. 4 (bottom). G9 treatment resulted in consistent suppression of MM1.S tumor growth in NSG mice. Control and treated mouse tumor sizes are shown on the left. Bars from left to right in each treatment group represent tumor size after 0, 4, 6, 8 and 11 days of treatment. Each bar represents the average+/−S.D. of measurements made in 3 mice per group. The significance of change in tumor volume between treated and control mice was calculated using GraphPad InStat. P-values<0.05 are considered significant. On the bottom, tumors were extracted from control and treated mice and photographed. Each row illustrates tumor from each of the three mice in the treatment group noted on the top of each row.

Figure 5:
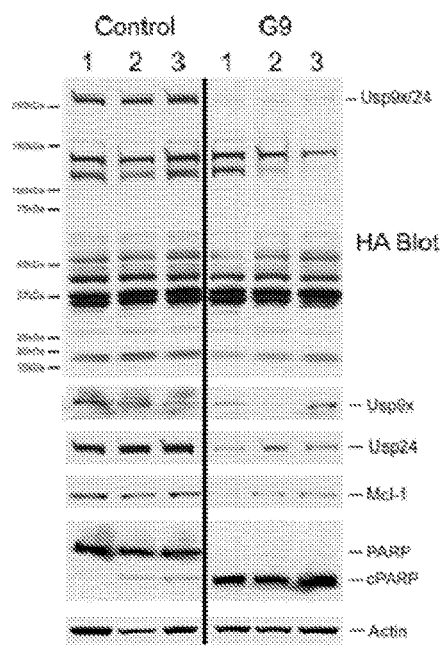
FIG. 5 shows Usp9x activity from protein extracts of control vs. G9 treated tumors.

The rapid onset of G9-mediated Usp9x inhibition short plasma half-life of G9 in mice suggests that Usp9x inhibition may be achievable in mice shortly after IP injection. To analyze that potential, mice were euthanized one hour after their last injection and tumors were extracted, photographed and flash-frozen on dry ice. Tumor tissue was sheared in liquid nitrogen, ground to a powder with a mortar and pestle and proteins extracted to assess Usp9x activity in 20 µg of protein from each tumor specimen. Tumors extracted from control and 15 mg/kg G9 treated mice were assessed for Usp9x activity as described above. The result of that analysis demonstrates Usp9x inhibition in mice treated with 15 mg/kg G9 (FIG. 5 right side) versus control mice (FIG. 5 left side). Also shown are the effects of treatment on Usp9x and Usp24 protein, the latter a DUB closely related to Usp9x. The effect of G9 on the Usp9x substrate Mcl-1, and on cleavage of caspase substrate PARP, are also shown. The results demonstrate that G9 reduces Usp9x DUB activity, reduces Mcl-1 protein levels and activates apoptosis in MM1.S tumors from NSG mice.

Figure 6:
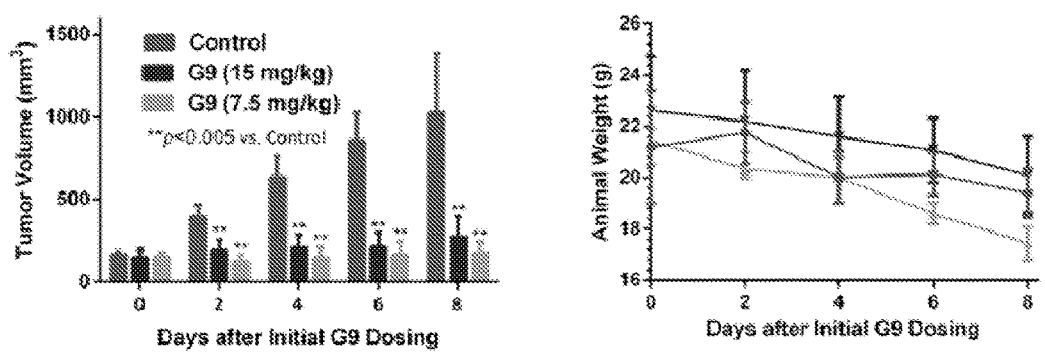
FIG. 6 shows the effect of G9 on A375 melanoma tumor growth and animal weight.

G9 suppresses Usp9x activity in A375 melanoma cells. The effect of G9 on the growth of A375 tumors in NSG mice was examined. Two million A375 cells in Matrigel: cell culture media (1:1) in 0.1 mL were injected subcutaneously in the dorsal region of 9 female NSG mice. After tumor growth to a measurable level (2 weeks post inoculation) animals were separated into 3 groups and mice received 0, 7.5 or 15 mg/kg G9 (prepared as described above) daily by IP injection for 8 days. Tumor volume (left) and animal weight (right) were measured every other day throughout the treatment interval and are reported in FIG. 6. G9 suppressed A375 tumor growth at either dose tested, with modest impact on animal weight. Three animals per treatment group were evaluated in this study. Each data point represents the average+/−S.D. of measurements made in three mice. P-values were calculated using GraphPad Instat. P-values<0.05 are considered significant.

To further evaluate the safety of G9, its apoptotic activity was compared in CD34+ cells (myeloid/lymphoid progenitors) derived from the blood of two normal (no known pathology) donors and two myeloma tumor cell lines (MM1.S, H929). Cellular apoptosis was measured by detection of annexin V on the surface of cells using flow cytometry. Cells were treated with the indicated concentration of G9 for 24 hours before assessing annexin positivity as an indication of cell survival using duplicate assays derived from duplicate samples. The average of 4 determinations+/−S.D. is reported in FIG. 7. CD34+ cells from two normal donors (left) or two myeloma cell lines (right) were treated with the indicated concentration of G9 for 24 hours before measuring cell survival by annexin V staining (assessed by flow cytometry). Each data point represents the average of 2 samples assayed in duplicate and presented as the average+/−S.D. for each G9 concentration. The results demonstrate that myeloma tumor cells are more apoptotically sensitive to G9 than normal CD34+ cells.

Usp9x is over-expressed or activated in a number of tumor cell types. G9 (and 067) inhibit Usp9x enzymatic activity and G9 inhibit Usp9x in intact tumor cells and is more effective than a previously described Usp9x inhibitor (WP1130). G9 suppresses Usp9x in tumors from tumor-bearing mice and reduces tumor growth (myeloma, melanoma) with tolerable changes in animal weight. G9 was more effective (~10-fold) in inducing apoptosis in tumor (myeloma) versus normal CD34+ cells.

Antiviral Activity of G9

Figure 8:
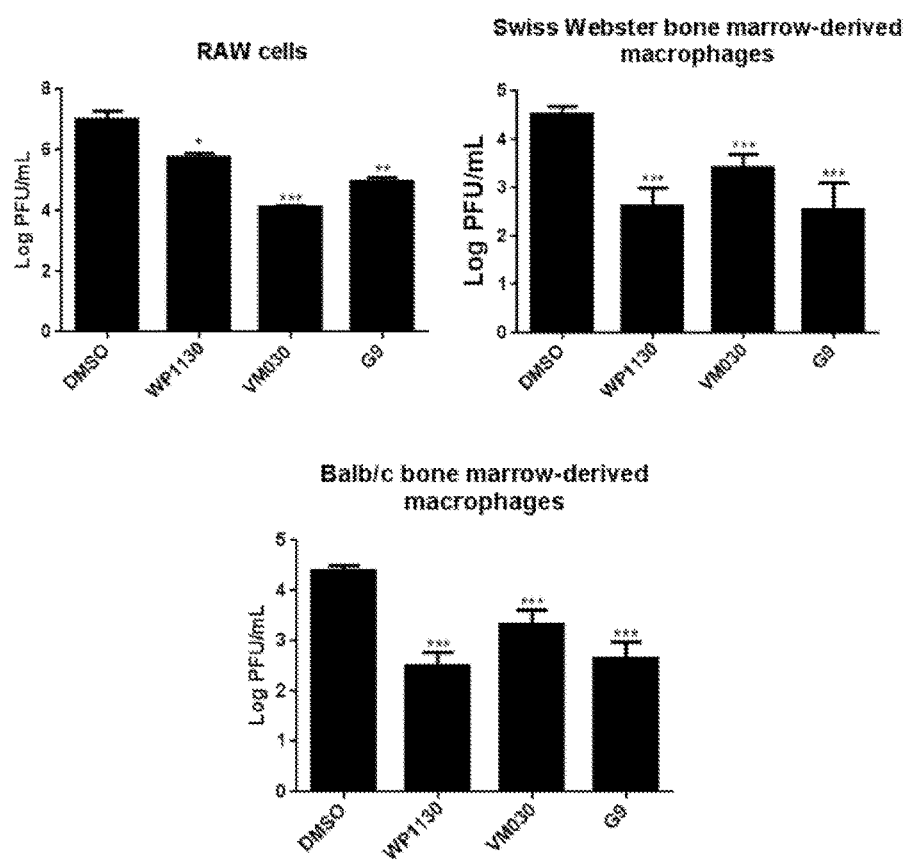
FIGS. 8 and 9 show antiviral activity in a variety of viruses and macrophages for G9, compared to vehicle (DMSO), prior compound WP1130 and compound VM030.

G9 was screened in RAW cells, Swiss Webster bone marrow derived macrophages and Balb/c bone marrow derived macrophages, compared to vehicle (DMSO), prior compound WP1130 and compound VM030. The results are shown in FIG. 8, showing G9 exhibits antiviral activity against murine norovirus in these various macrophages. VM030 has a structure of

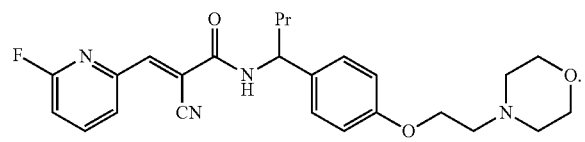

Figure 9:
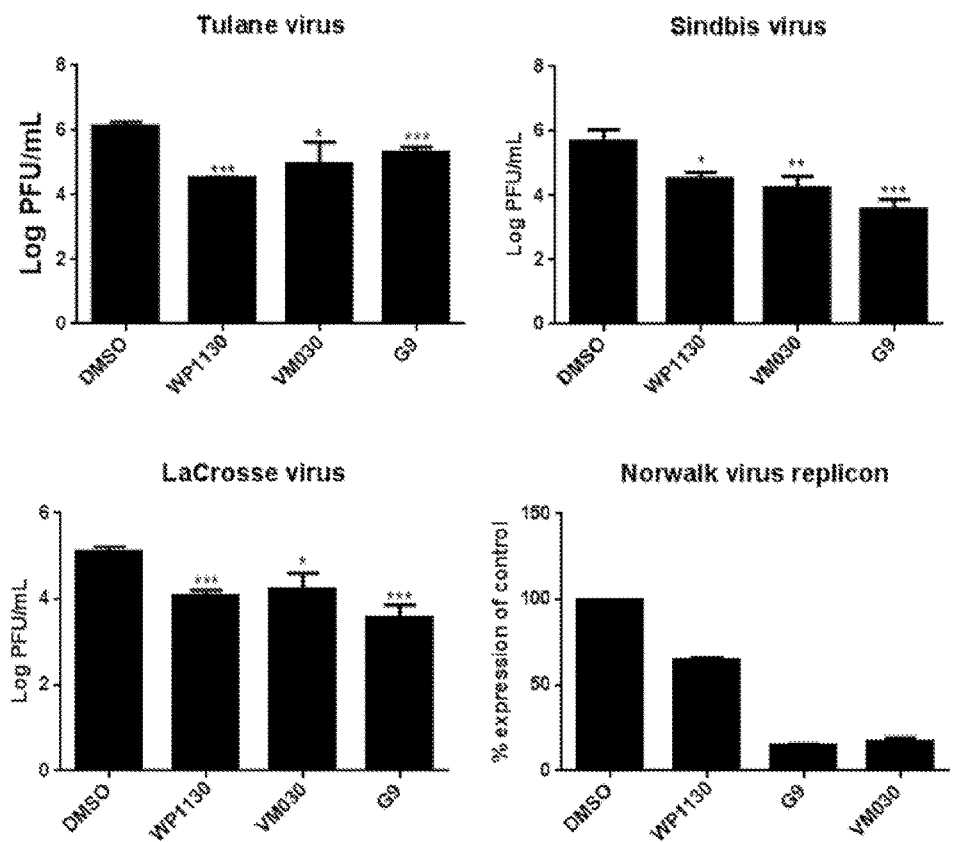
Figure 10:
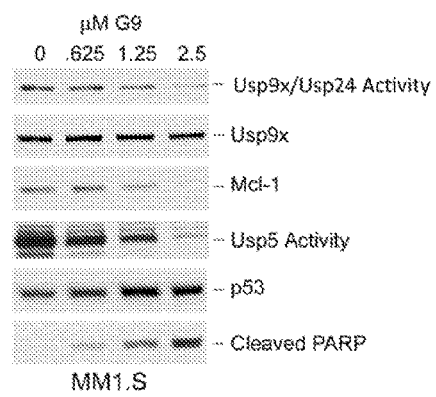
FIG. 10 shows G9 inhibits Usp9x and Usp5 in myeloma (MM1.S) cells at various concentrations.

These same compounds were screened in Vero cells against Sindbis virus, in LLC-MK cells against Tulane virus, in Be2-c cells against LaCrosse virus, and in Norwalk virus replicon-containing cells, all results shown in FIG. 9, and indicating that G9 exhibits mild to high antiviral activity against a variety of viruses.

Usp5, G9, and in Melanoma

Differential vemurafenib activity was confirmed in BRAF mutant (A375, SK-Mel-28) and non-mutant (SK-Mel-147) melanoma cell lines with regard to growth and pERK inhibition occurring only in BRAF mutant cells. Total protein ubiquitination was assessed in vemurafenib treated and control cells and it was noted that pERK inhibition was associated with an increase in total protein ubiquitination. Long-term exposures demonstrated that monomeric Ub was diminished while Ub polymers ($Ub_{2-4}$) were increased, consistent with previous reports of increased Ub polymers in DUB inhibited or knockdown cells (Dayal et al., J. Biol. Chem. 2009, 284(8):5030-5041). To determine whether DUB activity was affected by vemurafenib, melanoma cell lysates derived from control and treated cells were subjected to DUB activity assessment using an irreversible DUB inhibitor that covalently modifies active DUBs with HA-Ub. DUB activity was assessed by HA blotting and confirmed by monitoring a DUBs mobility shift due to its covalent modification with HA-Ub. DUB inhibition was detected in vemurafenib-responsive (SK-Mel28 and A375) cells and we noted a consistent change in a DUB (100 kDa) identified as Usp5 by LC/MS/MS of the excised protein band (data not shown) and direct immunoblotting. Vemurafenib did not alter Usp7 activity, a 130 kDa DUB previously shown to regulate p53 turnover. DUB activity was also compared in control and BRAF knockdown (KD) cells. BRAF shRNA reduced pERK levels and Usp5 activity. To confirm DUB regulation through BRAF activation, mutant BRAF (V600E) was expressed in HEK293T cells and DUB activity assessments used to demonstrate increased Usp5 activity in cells expressing $BRAF^{V600E}$. These results confirm that BRAF mutation or activation results in changes in the activity of specific DUBs, including Usp5.

Two mutant and two non-mutant BRAF melanoma cell lines were subjected to Usp5 KD and their growth kinetics were assessed over four days after plating equal numbers of initiating cells. Usp5 KD reduced the rate of growth of both BRAF mutant and non-mutant cells. Cell cycle analysis demonstrated that Usp5 is important for entry into G2/M. Growth inhibition was associated with induction of p21 in Usp5 KD cells and Usp5 KD caused >3-fold reduction in both the number and size of A375 colonies when plated on Matrigel, which partially replicates an in vivo 3D growth environment. Overexpression of Usp5 nearly doubled the rate of melanoma growth when compared to control cells.

To determine whether BRAF mediated-DUB activation regulates the cellular response to vemurafenib, control and Usp5 KD cells were treatment with vemurafenib for the interval indicated. Usp5 KD resulted in morphologic changes in A375 cells and >3-fold increased apoptotic responsiveness (annexin positivity) to vemurafenib in BRAF mutant cell lines. Usp5 was previously shown to regulate p53 entry into and destruction by the 20S proteasome (Dayal et al., J. Biol. Chem. 2009; 284(8):5030-5041). Usp5 KD resulted in increased levels of p53 protein and FAS in a panel of melanoma cells. Usp5 KD resulted in up-regulation of p53 in w/t p53 A375 cells and up-regulation of p73 in p53 mutant SK-Mel28 cells, suggesting that both proteins can be modulated by Usp5. In both w/t and mutant p53 expressing cells, Usp5 KD enhanced the onset or extent of apoptosis induced by vemurafenib, with evidence for activation of both the intrinsic and extrinsic pathway.

A375 control, Usp5 KD (Usp5 shRNA) and Usp5 over-expressing (Usp5 FLAG) cells were left untreated or treated with vemurafenib before examining Usp5 expression, activity, p53 protein levels and apoptosis. Usp5 KD and over-expression altered Usp5 DUB activity and its vemurafenib-mediated inhibition. Usp5 KD consistently led to p53 induction and accumulation of ubiquitinated p53 adducts, while Usp5 overexpression diminished p53 content. Vemurafenib did not alter Usp7 activity, which also regulates p53 levels in some cells. Increased p53 levels in Usp5 KD cells were associated with FAS induction and the rapid onset of apoptosis upon vemurafenib treatment. To assess the role of p53 induction in apoptosis and FAS regulation in cells with altered Usp5 expression, we compared apoptotic activity in cells with either Usp5 knockdown or dual knockdown of Usp5 and p53. Usp5 KD resulted in increased p53, FAS and Bax protein expression as well as increased Bid and PARP cleavage in response to vemurafenib. In dual Usp5/p53 KD cells, these activities were blocked, suggesting a prominent role for both Usp5 and p53 in the activation of vemurafenib-mediated cell death.

To confirm a role for Usp5 in FAS induction and function, control and Usp5 KD cells were treated with FAS-L and activation of the extrinsic apoptotic pathway was assessed. FAS-L resulted in limited activation of caspase 8, Bid and PARP cleavage, which was highly amplified by Usp5 KD. Similar results were obtained in cells treated with IFN-α, a FAS-inducing apoptotic cytokine used in the clinical treatment of melanoma. BRAF inhibition should release apoptotic suppression through reduced Usp5 activity, increased FAS expression and engagement of apoptosis, through the extrinsic caspase cascade. To test that potential, cells were treated with vemurafenib for extended intervals and assessed for FAS and Bax induction, caspase 8 activation, Bid and PARP cleavage. Vemurafenib treatment led to an early increase in protein ubiquitination, FAS and Bax induction (24 hours), followed by caspase 8, Bid and PARP cleavage after 48-72 hours. Vemurafenib reduced DR5 levels in SK-Mel19 cells, in agreement with previous studies (see, e.g., Oh et al., J. Biol. Chem., 2012; 287(1):257-267. BRAFV600E expression in HEK293T cells resulted in an increase in DR4 and DR5, but a reduction of FAS and p53 levels. FAS reduction by Usp5 appears to be mediated at the transcriptional level, possibly through down-regulation of p53 and other factors.

Since Usp5 was recently reported to play a role in DNA damage repair (see Nakajima et al., PloS one, 2014; 9(1): e84899), the effect of Usp5 KD on 5FU and Doxorubicin apoptotic responsiveness was assessed. Usp5 KD enhanced caspase activation, primarily through increased caspase 8 activation in both p53 wild-type and mutant cells. Usp5 also regulates p73 and may play a role in the apoptotic responsiveness of p53 mutant tumors (see Ozaki et al., Cancer science, 2005; 96(11):729-737).

To assess potential clinical relevance of Usp5 activity in melanoma, isogenic vemurafenib sensitive and resistant A375 melanoma cells were treated with G9. The effect of G9 on vemurafenib sensitive and resistant cells was assessed, and noted similar in vitro anti-tumor efficacy (IC$_{50}$ 1 μM). DUB activity in vemurafenib and G9 treated cells was compared and show that vemurafenib suppressed Usp5 activity in sensitive but not resistance cells, although pERK was reduced by kinase inhibitor in either cell type. Vemurafenib also failed to induce FAS in resistant cells. G9 reduced Usp5 (and Usp9x) activity in both cell types, increased p53 levels and retained pStat3 inhibitory activity as previously described for the WP1130 compound (see Kapuria et al., Cancer Res. 2010, 70(22):9265-9276; Bartholomeusz et al., Blood, 2007, 109(8):3470-3478; and Kapuria et al., Cell Signal, 2011, 23(12):2076-2085). To determine whether Usp5 KD (or G9) could overcome vemurafenib resistance, Usp5 KD A375R cells were left untreated or treated with vemurafenib (for 24 hrs) before assessing caspase activation, PARP and Bid cleavage. Usp5 KD enhanced p53 accumulation, increased FAS levels and activated apoptosis in response to vemurafenib. Similar results were obtained in A375R Usp5 KD cells treated with a MEK inhibitor. In addition, Usp5 KD reduced the vemurafenib IC$_{50}$ concentration in A375 cells by about 2-fold. In A375R cells, G9 reduced pERK, pStat3 and elevated NOXA levels, the latter related to Usp9x inhibition by G9. When combined with vemurafenib or 5FU, G9 induced PARP and Bid cleavage with activation of caspases 8 and 3.

A375 tumors grown as subcutaneous implants in NSG mice were separated into three groups and received once daily ip injections with vehicle control (PEG300/DMSO) or G9 at doses of 7.5 or 15 mg/kg. Tumor growth, animal weight, behavior and mobility were monitored during treatment. Both 7.5 and 15 mg/kg dosing completely suppressed tumor growth, with control mice reaching maximal tumor burden by day 8 of treatment. Cessation of G9 resulted in tumor growth which approached control levels 10 days after stopping G9 injection. Weight loss was not significantly different between control and G9 treated mice and we did not observe changes in behavior or mobility in control or G9 treated mice. These results suggest that G9 is well tolerated and effective as mono-therapy for melanoma.

What is claimed:

1. A compound having a formula (I):

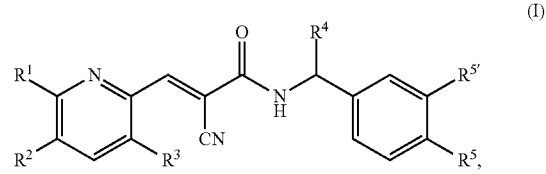

wherein
$R^1$ and $R^2$ together form an optionally substituted aryl ring or heteroaryl ring, and $R^3$ is halo or hydrogen;
$R^4$ is $C_2$-$C_6$alkyl or $C_1$-$C_6$alkylenearyl; and
(a) one of $R^5$ and $R^{5'}$ is hydrogen and the other substituted alkoxy, or (b) each of $R^5$ and $R^{5'}$ is substituted alkoxy, or (c) when the ring formed by $R^1$ and $R^2$ together is an aryl ring which is substituted, or is a heteroaryl ring which is optionally substituted, then $R^5$ and $R^{5'}$ can each be hydrogen;
or a salt or solvate thereof.

2. The compound of claim 1, wherein $R^1$ and $R^2$ together form a nitrogen-containing heteroaryl ring which is optionally substituted.

3. The compound of claim 2, wherein the compound of formula (I) has a structure

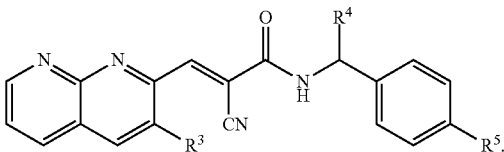

4. The compound of any one of claim 1, wherein $R^4$ is propyl or isopentyl.

5. The compound of claim 1, wherein $R^{5'}$ is hydrogen and $R^5$ is a heterocyclyl substituted alkoxy.

6. The compound of claim 5, wherein $R^5$ is —Oalkyleneheterocyclyl.

7. The compound of claim 1, wherein $R^5$ is hydrogen and $R^{5'}$ is a heterocyclyl substituted alkoxy.

8. The compound of claim 7, wherein $R^{5'}$ is —Oalkyleneheterocyclyl.

9. The compound of any one of claim 5, wherein the heterocyclyl is morpholinyl, sulfoxymorpholinyl, pyrrolidinyl, piperazinyl, or piperidinyl.

10. The compound of claim 9, wherein the heterocyclyl is morpholinyl.

11. The compound of claim 1, wherein $R^5$ or $R^{5'}$ is —O(CH$_2$)$_m$N(Me)(CH$_2$)$_2$NMe$_2$; —O(CH$_2$)$_m$N(Me)(CH$_2$)$_2$NHMe; —O(CH$_2$)$_m$N(Me)(CH$_2$)$_2$NEt$_2$; —O(CH$_2$)$_m$N(Me)(CH$_2$)$_2$NHEt; —O(CH$_2$)$_m$O(CH$_2$)$_2$NMe$_2$; —O(CH$_2$)$_m$O(CH$_2$)$_2$NHMe; —O(CH$_2$)$_m$O(CH$_2$)$_2$NEt$_2$; or —O(CH$_2$)$_m$O(CH$_2$)$_2$NHEt, and m is 1, 2, 3, 4, 5, 6, 7, 8, 9, or 10.

12. The compound of claim 1, wherein $R^3$ is chloro.

13. The compound of claim 1, wherein $R^3$ is fluoro.

14. A compound of having a structure

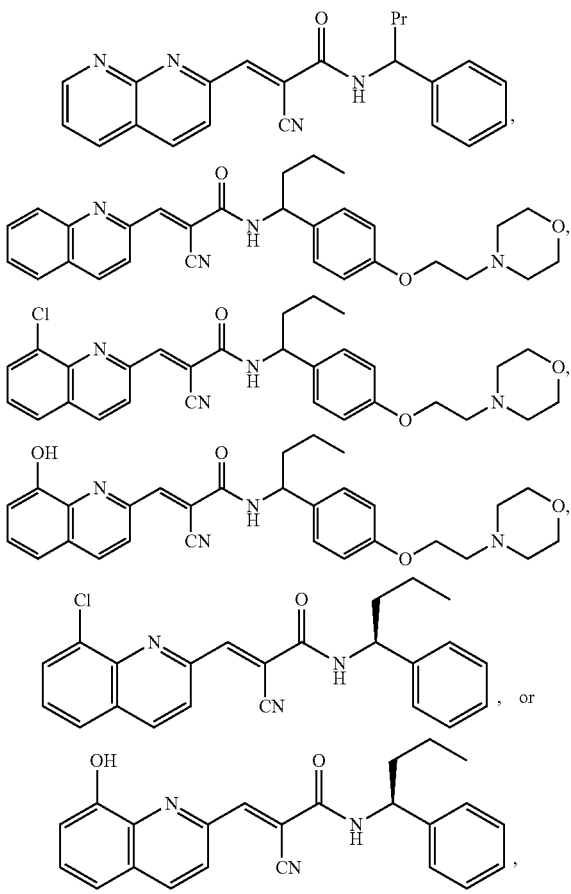

or a salt or solvate thereof.

15. A compound having a structure

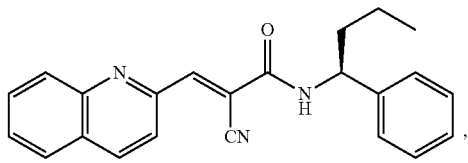 [SMILES: CCC[C@H](NC(=O)/C(C#N)=C/c1ccc2ccccc2n1)c1ccccc1]

or a salt or solvate thereof.

16. A method of inhibiting proliferation in a cancer cell, the method comprising contacting the cancer cell with the compound of claim 1 in an amount effective to inhibit proliferation, wherein the cancer cell is plasma cell leukemia, melanoma, or myeloma.

17. A method of inhibiting a deubiquitinase (DUB), the method comprising contacting a DUB with the compound of claim 1, wherein the DUB is Usp24 or Usp9x.

18. A compound having the structure

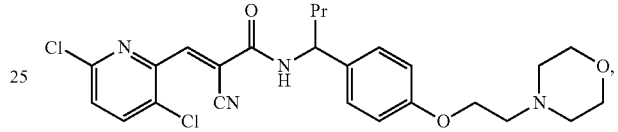

or a salt or solvate thereof.

19. A method of inhibiting proliferation in a cancer cell, the method comprising contacting the cancer cell with the compound of claim 18 in an amount effective to inhibit proliferation, wherein the cancer cell is plasma cell leukemia, melanoma, or myeloma.

20. A method of inhibiting a deubiquitinase (DUB), the method comprising contacting a DUB with the compound of claim 18, wherein the DUB is Usp24 or Usp9x.

21. A method of treating a viral infection, the method comprising contacting a cell infected with a virus with the compound of claim 18 in an amount effective to treat the viral infection, wherein the virus is a single stranded RNA virus.

22. A method of treating a viral infection, the method comprising contacting a cell infected with a virus with the compound of claim 18 in an amount effective to treat the viral infection, wherein the virus is a selected from the group consisting of: Tulane virus, Sindbis virus, LaCrosse virus, or Norwalk virus.

* * * * *

UNITED STATES PATENT AND TRADEMARK OFFICE
CERTIFICATE OF CORRECTION

Page 1 of 1

PATENT NO. : 9,868,736 B2
APPLICATION NO. : 15/027714
DATED : January 16, 2018
INVENTOR(S) : Nicholas J. Donato et al.

It is certified that error appears in the above-identified patent and that said Letters Patent is hereby corrected as shown below:

In the Claims

At Column 36, Line 53, "any one of claim" should be -- claim --.

At Column 36, Line 63, "any one of claim" should be -- claim --.

At Column 37, Line 10, "of having" should be -- having --.

At Column 38, Line 20, "having the" should be -- having a --.

Signed and Sealed this
Twenty-ninth Day of May, 2018

Andrei Iancu
*Director of the United States Patent and Trademark Office*